US009862962B2

(12) United States Patent
Messier

(10) Patent No.: US 9,862,962 B2
(45) Date of Patent: Jan. 9, 2018

(54) IDENTIFICATION AND USE OF TOMATO GENES CONTROLLING SALT/DROUGHT TOLERANCE AND FRUIT SWEETNESS

(71) Applicant: Evolutionary Genomics, Inc., Longmont, CO (US)

(72) Inventor: Walter Messier, Longmont, CO (US)

(73) Assignee: EG Corp Science, Inc., Longmont, CO (US)

(*) Notice: Subject to any disclaimer, the term of this patent is extended or adjusted under 35 U.S.C. 154(b) by 0 days.

(21) Appl. No.: 14/775,142

(22) PCT Filed: Mar. 14, 2014

(86) PCT No.: PCT/US2014/028764

§ 371 (c)(1),
(2) Date: Sep. 11, 2015

(87) PCT Pub. No.: WO2014/153032

PCT Pub. Date: Sep. 25, 2014

(65) Prior Publication Data

US 2016/0032306 A1 Feb. 4, 2016

Related U.S. Application Data

(60) Provisional application No. 61/783,288, filed on Mar. 14, 2013.

(51) Int. Cl.
*A01H 5/08* (2006.01)
*C12N 15/82* (2006.01)
*C07K 14/415* (2006.01)

(52) U.S. Cl.
CPC ........ *C12N 15/8245* (2013.01); *C07K 14/415* (2013.01); *C12N 15/8273* (2013.01)

(58) Field of Classification Search
None
See application file for complete search history.

(56) References Cited

U.S. PATENT DOCUMENTS 5,234,834 A 8/1993 Fischer et al.
5,914,446 A * 6/1999 Shewmaker ....... C12N 15/8245 435/320.1
2012/0102585 A1 4/2012 Heath et al.

OTHER PUBLICATIONS

Budiman et al. A deep-coverage tomato BAC library and prospects toward development of an STC framework for genome sequencing. Genome Res., Jan. 2000, pp. 129-136, vol. 10, No. 1.*
Kano-Murakami Y. et al. A rice homeotic gene, OSH1, causes unusual phenotypes in transgenic tobacco. FEBS Lett. Nov. 22, 1993;334(3):365-8.*
James et al. The relationship between homozygous and hemizygous transgene expression levels over generations in populations of transgenic rice plants. Theor. Appl. Genet. Mar. 2002;104(4):553-561.*
Budiman et al., "A deep-coverage tomato BAC library and prospects toward development of an STC framework for genome sequencing." Genome Res., Jan. 2000, pp. 129-136, vol. 10, No. 1.
Potato Genome Sequencing Consortium et al. "Genome sequence and analysis of the tuber crop potato.", Nature, Jul. 2011, pp. 189-195, vol. 475, No. 7355.
International Search Report, PCT application No. PCT/US2014/028764, dated Jul. 29, 2014, 5 pages.
M. D. Curtis, "A Gateway Cloning Vector Set for High-Throughput Functional Analysis of Genes in Planta", Plant Physiology, Sep. 11, 2003, pp. 462-469, vol. 133, No. 2.
Nookaraju A et al, "Molecular approaches for enhancing sweetness in fruits and vegetables", Scientia Horticulturae, Nov. 22, 2010, pp. 1-15, vol. 127, No. 1.
European Search Report, EP application No. 14769326.1, dated Jul. 20, 2016, 11 pages.
Balibrea, M. E. et al., "The high fruit soluble sugar content in wild Lycopersicon species and their hybrids with cultivars depends on sucrose import during ripening rather than on sucrose metabolism", Functional Plant Biology, Mar. 2, 2006, pp. 279-288, vol. 33, No. 3.
Database UniProt [Online] Nov. 28, 2012, SubName: Full=Uncharacterized protein {ECO:00003131EnsemblPiants:Solyc04g080300.2.1}, retrieved from EBI accession No. UNIPROT:K4BVA9, Database accession No. K4BVA9.
Kano-Murakami Y., et al., A rice homeotic gene, OSH1, causes unusual phenotypes in transgenic tobacco. FEBS Lett. Nov. 22, 1993; 334(3):365-368.
James et al., The relationship between homozygous and hemizygous transgene expression levels over generations in populations of transgenic rice plants. Theor. Appl. Genet. Mar. 2002; 104(4):553-561.
Written Opinion in International Application No. PCT/US2014/028764, dated Jul. 29, 2014, 5 pages.
International Preliminary Report on Patentability in International Application No. PCT/US2014/028764, dated Sep. 15, 2015, 6 pages.

* cited by examiner

*Primary Examiner* — Cynthia Collins
(74) *Attorney, Agent, or Firm* — Cooley LLP

(57) ABSTRACT

The present invention provides the identification and use of EGTom1 and/or EGTom2, homologs of EGTom1 and/or EGTom2, orthologs of EGTom1 and/or EGTom2, paralogs of EGTom1 and/or EGTom2, and fragments and variations thereof for altering salt tolerance, drought tolerance and/or sugar content of fruit (sweetness) in plants. The invention relates to the identification and use of nucleic acid sequences for salt/drought tolerance and fruit sweetness in plants.

14 Claims, 1 Drawing Sheet

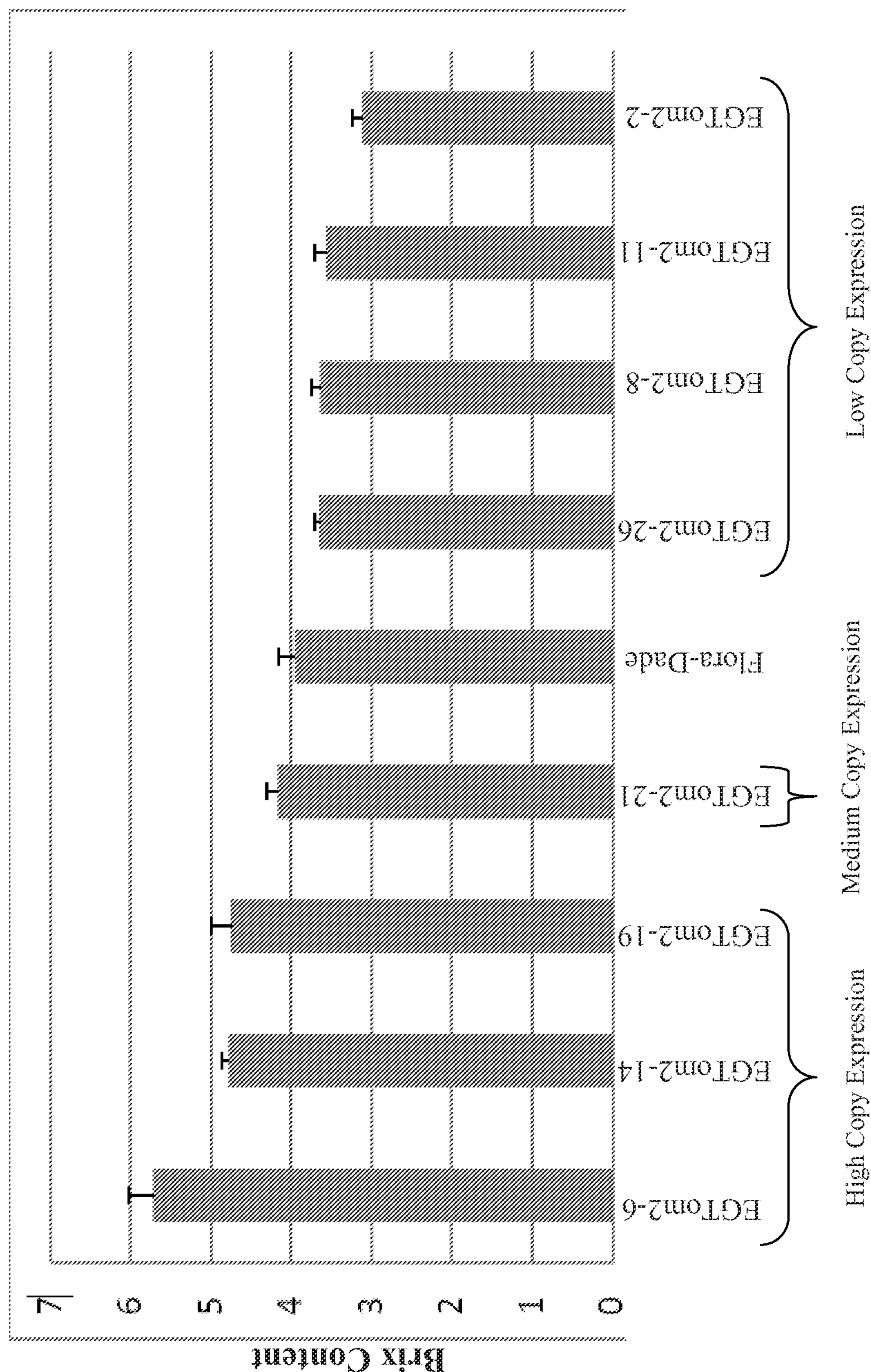
Brix Content
0
1
2
3
4
5
6
7
EGTom2-6
EGTom2-14
EGTom2-19
EGTom2-21
Flora-Dade
EGTom2-26
EGTom2-8
EGTom2-11
EGTom2-2
High Copy Expression
Medium Copy Expression
Low Copy Expression

SEQUENCE LISTING

<160> NUMBER OF SEQ ID NOS: 14

<210> SEQ ID NO 1
<211> LENGTH: 1767
<212> TYPE: DNA
<213> ORGANISM: Solanum chessmanii

<400> SEQUENCE: 1
atggagaata ataaaggaaa tgctgagagt aatgaggaca gtcatatcac acccagcacg 60
aagaaaactc acgcgcttca acaaaatggc gtggagaata tagaggcgcc ccccaactct 120
gatgcgacta aaaaaaaggg ccccagtaga agtgccaaga gaaaatctgc taaaagaaga 180
tggttgcgag agatggccaa aattaaggag aagaatgcag atgctgaatc ggaagggctg 240
cggaactgga aagaaatgca ggctaaagct ggaaagggag agcctagctg ccaaccaaag 300
gggcgattga atgacggggc taatggtcac cgaaatggga agcagcagaa aactaaaact 360
aaaaaagaag aggtaactgg ccaaccaaag ggacttctgc ataggaagca attccatagt 420
gaagataaga atggagatac aaacgaagaa aagcaagcag aagagaaaag caaatcatgt 480
ggacaatcat gtcaaaatag tgactcagaa gatgaagttg ttccagttga aataaggcct 540
gggcatattc gctttgaacc tgttggaaaa gaacaagttt caaagcagag tgaagaagaa 600

-continued

```
atggaaagtt tcaagtggaa tggtatgatg agcaagaaaa agggacagaa atggggccaa    660

gagaaagttt catttcccca aaagactgat tctctaggtt caaacaaaga atatcctgat    720

atgatgagtc gtgagagaca gaaatggatc caagagaaag actcattttc ccaaaagaat    780

gattccctta gttcaaacaa agaacatcct gagataatga atcgtaaaag acagaaatgg    840

ggccaagaga atatttcatt tgcccaaaag aatgattctc caggttcaag caaagaacat    900

cctgatatga tgaaccgtga gagacagaaa tggagccaag agaaaaactt gttttaccaa    960

aagaatgatt ctctcggttc aaacaaagaa catcccgaga taatgaatcg taatagacag   1020

aactggggcg aagagaatgt ttcattttcc caaaagaatg attctctaga ttcaaacaaa   1080

aaacatcctg agatgttgaa tggtgaaaag gagcctcatt tcaatggatc aattgacttc   1140

aatacacttc cttttctttc tggccagccc aaggaaggtc ttgtgattgc atatcggctg   1200

cttgagttat catcaacctg gacccctgaa gtttcctcct atcgggttgg gaaaatatca   1260

tcgtataatt ctgaagcaaa tagagttttg ctgatgccag tagctgaatt tccagtcatt   1320

tgtactgagg atgagtcttc aaagcaacca gatagctcta tttataatga agacggatct   1380

ttggagatag aattttcagc gcttcttgaa gttcgtctga tgaatagtac tccagatcaa   1440

ggagtacatg aaggggttat tgagggttct gctgccaatg agtccactcc agtgcttgga   1500

agcagtaaaa agaaaaatga aactccagtt cctggagctg gagaagtaag caatggaaaa   1560

caaacacgat ctaccccttc agaaaatggc ggagtaaacc tgtgggagca attcagtgat   1620

actctaaagt ccaagaaggc agaattagct caggaaagta attgggataa ggcaagtact   1680

ggaaagagcc cttggtcata tcgacccatg agaggcactg cgctaggccc tacaatggcc   1740

ttccttagat cccaaaagaa aatataa                                       1767
```

<210> SEQ ID NO 2
<211> LENGTH: 921
<212> TYPE: DNA
<213> ORGANISM: Solanum chessmanii

<400> SEQUENCE: 2

```
atggagaatt cgcgtgagtt tctaagcaat ggaaaaccag ctgatcctgg tcttcaaatt     60

ataaggcacc cctcttacca atcttgtggg aaattatcgt tatcttggtt tgatattaga    120

gtattttaca tcagaatcag caattttatg gtcgatgatt caaccccaga aattcttacg    180

cttaaccata tccctttaag ccccgataca ctgcttgaag ttaatggtat aagatgttca    240

gtgcactcgg aaggagcctc ttgctttctt cgaagggacc gtgttgataa gaaagctgaa    300

gaagctacat ttgtgagcac agatagtata agattgactg ggagtgtgaa ctttgaggtt    360

tcatataaag atgatctttt tctctctggg actttggaga tggccaacat caatgattct    420

caaaactgtc ttaggagatg gagcatgaac tgtgaatcag ttatgagtgc tggcacggga    480

tttctgaaag gaaaacatat tgtgggttct gaatcattgt caccgacaat tgaagtctat    540

gttaccggtt gcttctctgg gacacctatc atcttaacta agactttgca gctaaatcac    600

aggaagaagc accatagaaa gggtatgtta gactccattc cggagcatga cacttctgaa    660

cagcataaag aagtctcatc tgaacatgat ctgcaggtaa cagaatacaa cggaaactac    720

aaaccagaaa gcgaagaaga ctacaacaac atgtactggg gacgaacaga acttatggat    780

ggtgaagacg gagaaatgtc ctggttcaat gctggggttc gagttggtgt tgggattggc    840

cttggcattt gtgtaggagt tggagtagga gttggtttat tagtccgtac tacacgcaac    900

ttaagaaggc gccttatgta a                                              921
```

<210> SEQ ID NO 3
<211> LENGTH: 1846
<212> TYPE: DNA
<213> ORGANISM: Solanum esculentum

<400> SEQUENCE: 3

```
atggagaata ataaaggaaa tgctgagagt aatgaggaca gtcatatcac acccagcacg     60
aagaaaactc acgcgcttca acaaaatggc gtggagaata tagaggtgcc ccccaactct    120
gatgcgacta aaaaaaaggg ccccagtaga agtgccaaga gaaaatctgc taaaaggcga    180
tggttgcgag agatggccaa aattaaggag aagaatgcag atgctgaatc ggaagggctg    240
cggaactgga aagaaatgca ggctaaagct ggaaagggag agcctagctg ccaaccaaag    300
gggcgattga atgacggggc taatggtcac cgaaatggga agcagcagat aactaaaact    360
aaaaaagaag aggtaactgg ccaaccaaag ggacttctgc ataggaagca attccatagt    420
gaagataaga atggagatac aaacgaagaa aagcaagcag aagagaaaag caaatcatgt    480
ggacaatcat gtcaaaatag tgactcagaa gatgaagttg ttccagttga aataaggcct    540
gggcatattc gctttgaacc tgttggaaaa gaacaagttt caaagcagag tcaagaagaa    600
atggaaagtt tcaagtggaa tggtatgatg agcaagaaaa agggacagaa atggggccaa    660
gagaaagttt catttcccca aaagactgat tctctaggtt caaacaaaga atatcctgat    720
atgatgagtc gtgagagaca gaaatggatc caagagaaag actcattttc ccaaaagaat    780
gattccctta gttcaaacaa agaacatcct gagataatga atcgtaaaag acagaaatgg    840
ggccaagaga atatttcatt tgcccaaaag aatgattctc caggttcaag caaagaacat    900
cctgatatga tgaaccgtga gagacagaaa tggagccaag agaaaaactt gttttaccaa    960
aagaatgatt ctctcggttc aaacaaagaa catcccgaga taatgaatcg taatagacag   1020
aactggggcg aagagaatgt ttcattttcc caaaagaatg attctctaga ttcaaacaaa   1080
aaacatcctg agatgttgaa tggtgaaaag gagcctcatt tcaatggatc aattgacttc   1140
aatacgcttc cttttctttc tggccagccc aaggaaggtc ttgtgattgc atatcggctg   1200
cttgagttat catcaacctg gacccctgaa gtttcctcct atcgggttgg gaaaatatca   1260
tcgtataatt ctgaagcaaa tagagttttg ctgatgccag tagctgaatt tccagtcatt   1320
tgtactgagg atgagtcttc aaagcaacca gatagctcta tttataatga agacggatct   1380
ttggagatag aattttcagc gcttcttgaa gttcgtctga tgaatagtac tccagatcaa   1440
ggagtacatg aaggggttat tgagggttct gctgccaatg agtccactcc agtgcttgga   1500
agcagtaaaa agaaaaatga aactccagtt cctggagctg gagaagtaag caatggaaaa   1560
caaacacgat ctaccccttc agaaaatggc ggagtaaacc tgtgggagca attcagtgat   1620
actctaaagt ccaagaaggc agaattagct caggaaagta attgggataa ggcaagtact   1680
ggaaagagcc cttggtcata tcgacccatg agaggcactg cgctaggccc tacaatggcc   1740
ttccttagat cccaaaagaa aatataagat gaagttgcag ttgcatattt tgttcatatt   1800
atcgtatatt aacccgtttc attctcttta agttttgcaa aattct                  1846
```

<210> SEQ ID NO 4
<211> LENGTH: 1767
<212> TYPE: DNA
<213> ORGANISM: Solanum esculentum

<400> SEQUENCE: 4

```
atggagaata ataaaggaaa tgctgagagt aatgaggaca gtcatatcac acccagcacg     60
aagaaaactc acgcgcttca acaaaatggc gtggagaata tagaggtgcc ccccaactct    120
gatgcgacta aaaaaaaggg ccccagtaga agtgccaaga gaaaatctgc taaaaggcga    180
tggttgcgag agatggccaa aattaaggag aagaatgcag atgctgaatc ggaagggctg    240
cggaactgga aagaaatgca ggctaaagct ggaaagggag agcctagctg ccaaccaaag    300
gggcgattga atgacggggc taatggtcac cgaaatggga agcagcagat aactaaaact    360
aaaaaagaag aggtaactgg ccaaccaaag ggacttctgc ataggaagca attccatagt    420
gaagataaga atggagatac aaacgaagaa aagcaagcag aagagaaaag caaatcatgt    480
ggacaatcat gtcaaaatag tgactcagaa gatgaagttg ttccagttga aataaggcct    540
gggcatattc gctttgaacc tgttggaaaa gaacaagttt caaagcagag tcaagaagaa    600
atggaaagtt tcaagtggaa tggtatgatg agcaagaaaa agggacagaa atggggccaa    660
gagaaagttt catttcccca aaagactgat tctctaggtt caaacaaaga atatcctgat    720
atgatgagtc gtgagagaca gaaatggatc caagagaaag actcattttc ccaaaagaat    780
gattccctta gttcaaacaa agaacatcct gagataatga atcgtaaaag acagaaatgg    840
ggccaagaga atatttcatt tgcccaaaag aatgattctc caggttcaag caaagaacat    900
cctgatatga tgaaccgtga gagacagaaa tggagccaag agaaaaactt gttttaccaa    960
aagaatgatt ctctcggttc aaacaaagaa catcccgaga taatgaatcg taatagacag   1020
aactggggcg aagagaatgt ttcattttcc caaaagaatg attctctaga ttcaaacaaa   1080
aaacatcctg agatgttgaa tggtgaaaag gagcctcatt tcaatggatc aattgacttc   1140
aatacgcttc cttttctttc tggccagccc aaggaaggtc ttgtgattgc atatcggctg   1200
cttgagttat catcaacctg gacccctgaa gtttcctcct atcgggttgg gaaaatatca   1260
tcgtataatt ctgaagcaaa tagagttttg ctgatgccag tagctgaatt tccagtcatt   1320
tgtactgagg atgagtcttc aaagcaacca gatagctcta tttataatga agacggatct   1380
ttggagatag aattttcagc gcttcttgaa gttcgtctga tgaatagtac tccagatcaa   1440
ggagtacatg aaggggttat tgagggttct gctgccaatg agtccactcc agtgcttgga   1500
agcagtaaaa agaaaaatga aactccagtt cctggagctg gagaagtaag caatggaaaa   1560
caaacacgat ctaccccttc agaaaatggc ggagtaaacc tgtgggagca attcagtgat   1620
actctaaagt ccaagaaggc agaattagct caggaaagta attgggataa ggcaagtact   1680
ggaaagagcc cttggtcata tcgacccatg agaggcactg cgctaggccc tacaatggcc   1740
ttccttagat cccaaaagaa aatataa                                       1767
```

```
<210> SEQ ID NO 5
<211> LENGTH: 1013
<212> TYPE: DNA
<213> ORGANISM: Solanum esculentum

<400> SEQUENCE: 5

catggtgaag gattttagtg agggataaga agctacgata tatggagaat tcgcgtgagt     60
ttctaagcaa tggaaaacca gctgatcctg gtcttcaaat tataaggcac ccctcttacc    120
aatcttgtgg gaaattatcg ttatcttggt ttgatattag agtcttttac atcagaatca    180
gcaattttat ggtcgatgat tcaaccccag aaagtcttac gcttaaccat atccctctaa    240
gccccgatac actgcttgaa gttaatggta aaagatgttc agtgtactca gaaggagcct    300
cttgctttct tcgaagggac cgtgttgata agaaagctga agaagctaca tttgtgagca    360
```

```
cagatagtat aagattgact gggagtgtga actttgaggt ttcatataaa gatgatcttt    420
ttctctctgg gactttggag atggccaaca tcaatgattc tcaaaactgt cttaggagat    480
ggagcatgaa ctgtgaatca gttatgagtg ctggcacggg atttctgaaa ggaaaacata    540
ttgtgggttc tgaatcattg tcaccgacaa ttgaagtgta tgttactggt tgcttctctg    600
ggacacctat catcttaact aagactttgc agctaaatca caggaagaag caccatagaa    660
agggtatgtt ggactccatt ccggagcatg acacatctga acagcataaa gaagtctcat    720
ctgaacatga tctgcaggta acagaataca acggaaacta caaaccagaa agcgaagaag    780
actacaacaa catgtactgg ggacgaacag aacttatgga tggtgaagac ggagaaatgt    840
cctggttcaa tgctggggtt cgagttggtg ttgggattgg ccttggcatt tgtgtaggag    900
ttggagtagg agttggttta ttagtccgta ctacacgaaa cttaagaagg cgccttatgt    960
aattacatag catacatata aaaggctaac aatacagaga tgctgttttt aag         1013
```

<210> SEQ ID NO 6
<211> LENGTH: 921
<212> TYPE: DNA
<213> ORGANISM: Solanum esculentum

<400> SEQUENCE: 6

```
atggagaatt cgcgtgagtt tctaagcaat ggaaaaccag ctgatcctgg tcttcaaatt     60
ataaggcacc cctcttacca atcttgtggg aaattatcgt tatcttggtt tgatattaga    120
gtcttttaca tcagaatcag caattttatg gtcgatgatt caaccccaga aagtcttacg    180
cttaaccata tccctctaag ccccgataca ctgcttgaag ttaatggtaa aagatgttca    240
gtgtactcag aaggagcctc ttgctttctt cgaagggacc gtgttgataa gaaagctgaa    300
gaagctacat ttgtgagcac agatagtata agattgactg ggagtgtgaa ctttgaggtt    360
tcatataaag atgatctttt tctctctggg actttggaga tggccaacat caatgattct    420
caaaactgtc ttaggagatg gagcatgaac tgtgaatcag ttatgagtgc tggcacggga    480
tttctgaaag gaaaacatat tgtgggttct gaatcattgt caccgacaat tgaagtgtat    540
gttactggtt gcttctctgg gacacctatc atcttaacta agactttgca gctaaatcac    600
aggaagaagc accatagaaa gggtatgttg gactccattc cggagcatga cacatctgaa    660
cagcataaag aagtctcatc tgaacatgat ctgcaggtaa cagaatacaa cggaaactac    720
aaaccagaaa gcgaagaaga ctacaacaac atgtactggg gacgaacaga acttatggat    780
ggtgaagacg gagaaatgtc ctggttcaat gctggggttc gagttggtgt tgggattggc    840
cttggcattt gtgtaggagt tggagtagga gttggtttat tagtccgtac tacacgaaac    900
ttaagaaggc gccttatgta a                                              921
```

<210> SEQ ID NO 7
<211> LENGTH: 588
<212> TYPE: PRT
<213> ORGANISM: Solanum chessmanii

<400> SEQUENCE: 7

```
Met Glu Asn Asn Lys Gly Asn Ala Glu Ser Asn Glu Asp Ser His Ile
1               5                   10                  15

Thr Pro Ser Thr Lys Lys Thr His Ala Leu Gln Gln Asn Gly Val Glu
            20                  25                  30

Asn Ile Glu Ala Pro Pro Asn Ser Asp Ala Thr Lys Lys Lys Gly Pro
        35                  40                  45
```

```
Ser Arg Ser Ala Lys Arg Lys Ser Ala Lys Arg Arg Trp Leu Arg Glu
    50                  55                  60

Met Ala Lys Ile Lys Glu Lys Asn Ala Asp Ala Glu Ser Glu Gly Leu
65                  70                  75                  80

Arg Asn Trp Lys Glu Met Gln Ala Lys Ala Gly Lys Gly Glu Pro Ser
                85                  90                  95

Cys Gln Pro Lys Gly Arg Leu Asn Asp Gly Ala Asn Gly His Arg Asn
            100                 105                 110

Gly Lys Gln Gln Lys Thr Lys Thr Lys Lys Glu Glu Val Thr Gly Gln
        115                 120                 125

Pro Lys Gly Leu Leu His Arg Lys Gln Phe His Ser Glu Asp Lys Asn
    130                 135                 140

Gly Asp Thr Asn Glu Glu Lys Gln Ala Glu Glu Lys Ser Lys Ser Cys
145                 150                 155                 160

Gly Gln Ser Cys Gln Asn Ser Asp Ser Glu Asp Glu Val Val Pro Val
                165                 170                 175

Glu Ile Arg Pro Gly His Ile Arg Phe Glu Pro Val Gly Lys Glu Gln
            180                 185                 190

Val Ser Lys Gln Ser Glu Glu Glu Met Glu Ser Phe Lys Trp Asn Gly
        195                 200                 205

Met Met Ser Lys Lys Lys Gly Gln Lys Trp Gly Gln Glu Lys Val Ser
    210                 215                 220

Phe Pro Gln Lys Thr Asp Ser Leu Gly Ser Asn Lys Glu Tyr Pro Asp
225                 230                 235                 240

Met Met Ser Arg Glu Arg Gln Lys Trp Ile Gln Glu Lys Asp Ser Phe
                245                 250                 255

Ser Gln Lys Asn Asp Ser Leu Ser Ser Asn Lys Glu His Pro Glu Ile
            260                 265                 270

Met Asn Arg Lys Arg Gln Lys Trp Gly Gln Glu Asn Ile Ser Phe Ala
        275                 280                 285

Gln Lys Asn Asp Ser Pro Gly Ser Ser Lys Glu His Pro Asp Met Met
    290                 295                 300

Asn Arg Glu Arg Gln Lys Trp Ser Gln Glu Lys Asn Leu Phe Tyr Gln
305                 310                 315                 320

Lys Asn Asp Ser Leu Gly Ser Asn Lys Glu His Pro Glu Ile Met Asn
                325                 330                 335

Arg Asn Arg Gln Asn Trp Gly Glu Glu Asn Val Ser Phe Ser Gln Lys
            340                 345                 350

Asn Asp Ser Leu Asp Ser Asn Lys Lys His Pro Glu Met Leu Asn Gly
        355                 360                 365

Glu Lys Glu Pro His Phe Asn Gly Ser Ile Asp Phe Asn Thr Leu Pro
    370                 375                 380

Phe Leu Ser Gly Gln Pro Lys Glu Gly Leu Val Ile Ala Tyr Arg Leu
385                 390                 395                 400

Leu Glu Leu Ser Ser Thr Trp Thr Pro Glu Val Ser Ser Tyr Arg Val
                405                 410                 415

Gly Lys Ile Ser Ser Tyr Asn Ser Glu Ala Asn Arg Val Leu Leu Met
            420                 425                 430

Pro Val Ala Glu Phe Pro Val Ile Cys Thr Glu Asp Glu Ser Ser Lys
        435                 440                 445

Gln Pro Asp Ser Ser Ile Tyr Asn Glu Asp Gly Ser Leu Glu Ile Glu
    450                 455                 460
```

```
Phe Ser Ala Leu Leu Glu Val Arg Leu Met Asn Ser Thr Pro Asp Gln
465                 470                 475                 480

Gly Val His Glu Gly Val Ile Glu Gly Ser Ala Ala Asn Glu Ser Thr
                485                 490                 495

Pro Val Leu Gly Ser Ser Lys Lys Lys Asn Glu Thr Pro Val Pro Gly
            500                 505                 510

Ala Gly Glu Val Ser Asn Gly Lys Gln Thr Arg Ser Thr Pro Ser Glu
        515                 520                 525

Asn Gly Gly Val Asn Leu Trp Glu Gln Phe Ser Asp Thr Leu Lys Ser
    530                 535                 540

Lys Lys Ala Glu Leu Ala Gln Glu Ser Asn Trp Asp Lys Ala Ser Thr
545                 550                 555                 560

Gly Lys Ser Pro Trp Ser Tyr Arg Pro Met Arg Gly Thr Ala Leu Gly
                565                 570                 575

Pro Thr Met Ala Phe Leu Arg Ser Gln Lys Lys Ile
            580                 585


<210> SEQ ID NO 8
<211> LENGTH: 306
<212> TYPE: PRT
<213> ORGANISM: Solanum chessmanii

<400> SEQUENCE: 8

Met Glu Asn Ser Arg Glu Phe Leu Ser Asn Gly Lys Pro Ala Asp Pro
1               5                   10                  15

Gly Leu Gln Ile Ile Arg His Pro Ser Tyr Gln Ser Cys Gly Lys Leu
            20                  25                  30

Ser Leu Ser Trp Phe Asp Ile Arg Val Phe Tyr Ile Arg Ile Ser Asn
        35                  40                  45

Phe Met Val Asp Asp Ser Thr Pro Glu Ile Leu Thr Leu Asn His Ile
    50                  55                  60

Pro Leu Ser Pro Asp Thr Leu Leu Glu Val Asn Gly Ile Arg Cys Ser
65                  70                  75                  80

Val His Ser Glu Gly Ala Ser Cys Phe Leu Arg Arg Asp Arg Val Asp
                85                  90                  95

Lys Lys Ala Glu Glu Ala Thr Phe Val Ser Thr Asp Ser Ile Arg Leu
            100                 105                 110

Thr Gly Ser Val Asn Phe Glu Val Ser Tyr Lys Asp Asp Leu Phe Leu
        115                 120                 125

Ser Gly Thr Leu Glu Met Ala Asn Ile Asn Asp Ser Gln Asn Cys Leu
    130                 135                 140

Arg Arg Trp Ser Met Asn Cys Glu Ser Val Met Ser Ala Gly Thr Gly
145                 150                 155                 160

Phe Leu Lys Gly Lys His Ile Val Gly Ser Glu Ser Leu Ser Pro Thr
                165                 170                 175

Ile Glu Val Tyr Val Thr Gly Cys Phe Ser Gly Thr Pro Ile Ile Leu
            180                 185                 190

Thr Lys Thr Leu Gln Leu Asn His Arg Lys Lys His His Arg Lys Gly
        195                 200                 205

Met Leu Asp Ser Ile Pro Glu His Asp Thr Ser Glu Gln His Lys Glu
    210                 215                 220

Val Ser Ser Glu His Asp Leu Gln Val Thr Glu Tyr Asn Gly Asn Tyr
225                 230                 235                 240

Lys Pro Glu Ser Glu Glu Asp Tyr Asn Asn Met Tyr Trp Gly Arg Thr
                245                 250                 255
```

```
Glu Leu Met Asp Gly Glu Asp Gly Glu Met Ser Trp Phe Asn Ala Gly
            260                 265                 270

Val Arg Val Gly Val Gly Ile Gly Leu Gly Ile Cys Val Gly Val Gly
        275                 280                 285

Val Gly Val Gly Leu Leu Val Arg Thr Thr Arg Asn Leu Arg Arg Arg
    290                 295                 300

Leu Met
305


<210> SEQ ID NO 9
<211> LENGTH: 588
<212> TYPE: PRT
<213> ORGANISM: Solanum esculentum

<400> SEQUENCE: 9

Met Glu Asn Asn Lys Gly Asn Ala Glu Ser Asn Glu Asp Ser His Ile
1               5                   10                  15

Thr Pro Ser Thr Lys Lys Thr His Ala Leu Gln Gln Asn Gly Val Glu
            20                  25                  30

Asn Ile Glu Val Pro Pro Asn Ser Asp Ala Thr Lys Lys Lys Gly Pro
        35                  40                  45

Ser Arg Ser Ala Lys Arg Lys Ser Ala Lys Arg Arg Trp Leu Arg Glu
    50                  55                  60

Met Ala Lys Ile Lys Glu Lys Asn Ala Asp Ala Glu Ser Glu Gly Leu
65                  70                  75                  80

Arg Asn Trp Lys Glu Met Gln Ala Lys Ala Gly Lys Gly Glu Pro Ser
                85                  90                  95

Cys Gln Pro Lys Gly Arg Leu Asn Asp Gly Ala Asn Gly His Arg Asn
            100                 105                 110

Gly Lys Gln Gln Ile Thr Lys Thr Lys Lys Glu Glu Val Thr Gly Gln
        115                 120                 125

Pro Lys Gly Leu Leu His Arg Lys Gln Phe His Ser Glu Asp Lys Asn
    130                 135                 140

Gly Asp Thr Asn Glu Glu Lys Gln Ala Glu Glu Lys Ser Lys Ser Cys
145                 150                 155                 160

Gly Gln Ser Cys Gln Asn Ser Asp Ser Glu Asp Glu Val Val Pro Val
                165                 170                 175

Glu Ile Arg Pro Gly His Ile Arg Phe Glu Pro Val Gly Lys Glu Gln
            180                 185                 190

Val Ser Lys Gln Ser Gln Glu Glu Met Glu Ser Phe Lys Trp Asn Gly
        195                 200                 205

Met Met Ser Lys Lys Lys Gly Gln Lys Trp Gly Gln Glu Lys Val Ser
    210                 215                 220

Phe Pro Gln Lys Thr Asp Ser Leu Gly Ser Asn Lys Glu Tyr Pro Asp
225                 230                 235                 240

Met Met Ser Arg Glu Arg Gln Lys Trp Ile Gln Glu Lys Asp Ser Phe
                245                 250                 255

Ser Gln Lys Asn Asp Ser Leu Ser Ser Asn Lys Glu His Pro Glu Ile
            260                 265                 270

Met Asn Arg Lys Arg Gln Lys Trp Gly Gln Glu Asn Ile Ser Phe Ala
        275                 280                 285

Gln Lys Asn Asp Ser Pro Gly Ser Ser Lys Glu His Pro Asp Met Met
    290                 295                 300

Asn Arg Glu Arg Gln Lys Trp Ser Gln Glu Lys Asn Leu Phe Tyr Gln
```

```
305                 310                 315                 320

Lys Asn Asp Ser Leu Gly Ser Asn Lys Glu His Pro Glu Ile Met Asn
                325                 330                 335

Arg Asn Arg Gln Asn Trp Gly Glu Glu Asn Val Ser Phe Ser Gln Lys
            340                 345                 350

Asn Asp Ser Leu Asp Ser Asn Lys Lys His Pro Glu Met Leu Asn Gly
        355                 360                 365

Glu Lys Glu Pro His Phe Asn Gly Ser Ile Asp Phe Asn Thr Leu Pro
    370                 375                 380

Phe Leu Ser Gly Gln Pro Lys Glu Gly Leu Val Ile Ala Tyr Arg Leu
385                 390                 395                 400

Leu Glu Leu Ser Ser Thr Trp Thr Pro Glu Val Ser Ser Tyr Arg Val
                405                 410                 415

Gly Lys Ile Ser Ser Tyr Asn Ser Glu Ala Asn Arg Val Leu Leu Met
            420                 425                 430

Pro Val Ala Glu Phe Pro Val Ile Cys Thr Glu Asp Glu Ser Ser Lys
        435                 440                 445

Gln Pro Asp Ser Ser Ile Tyr Asn Glu Asp Gly Ser Leu Glu Ile Glu
    450                 455                 460

Phe Ser Ala Leu Leu Glu Val Arg Leu Met Asn Ser Thr Pro Asp Gln
465                 470                 475                 480

Gly Val His Glu Gly Val Ile Glu Gly Ser Ala Ala Asn Glu Ser Thr
                485                 490                 495

Pro Val Leu Gly Ser Ser Lys Lys Lys Asn Glu Thr Pro Val Pro Gly
            500                 505                 510

Ala Gly Glu Val Ser Asn Gly Lys Gln Thr Arg Ser Thr Pro Ser Glu
        515                 520                 525

Asn Gly Gly Val Asn Leu Trp Glu Gln Phe Ser Asp Thr Leu Lys Ser
    530                 535                 540

Lys Lys Ala Glu Leu Ala Gln Glu Ser Asn Trp Asp Lys Ala Ser Thr
545                 550                 555                 560

Gly Lys Ser Pro Trp Ser Tyr Arg Pro Met Arg Gly Thr Ala Leu Gly
                565                 570                 575

Pro Thr Met Ala Phe Leu Arg Ser Gln Lys Lys Ile
            580                 585


<210> SEQ ID NO 10
<211> LENGTH: 588
<212> TYPE: PRT
<213> ORGANISM: Solanum esculentum

<400> SEQUENCE: 10

Met Glu Asn Asn Lys Gly Asn Ala Glu Ser Asn Glu Asp Ser His Ile
1               5                   10                  15

Thr Pro Ser Thr Lys Lys Thr His Ala Leu Gln Gln Asn Gly Val Glu
            20                  25                  30

Asn Ile Glu Val Pro Pro Asn Ser Asp Ala Thr Lys Lys Lys Gly Pro
        35                  40                  45

Ser Arg Ser Ala Lys Arg Lys Ser Ala Lys Arg Arg Trp Leu Arg Glu
    50                  55                  60

Met Ala Lys Ile Lys Glu Lys Asn Ala Asp Ala Glu Ser Glu Gly Leu
65                  70                  75                  80

Arg Asn Trp Lys Glu Met Gln Ala Lys Ala Gly Lys Gly Glu Pro Ser
                85                  90                  95
```

```
Cys Gln Pro Lys Gly Arg Leu Asn Asp Gly Ala Asn Gly His Arg Asn
            100                 105                 110

Gly Lys Gln Gln Ile Thr Lys Thr Lys Lys Glu Glu Val Thr Gly Gln
        115                 120                 125

Pro Lys Gly Leu Leu His Arg Lys Gln Phe His Ser Glu Asp Lys Asn
    130                 135                 140

Gly Asp Thr Asn Glu Glu Lys Gln Ala Glu Glu Lys Ser Lys Ser Cys
145                 150                 155                 160

Gly Gln Ser Cys Gln Asn Ser Asp Ser Glu Asp Glu Val Val Pro Val
                165                 170                 175

Glu Ile Arg Pro Gly His Ile Arg Phe Glu Pro Val Gly Lys Glu Gln
            180                 185                 190

Val Ser Lys Gln Ser Gln Glu Glu Met Glu Ser Phe Lys Trp Asn Gly
        195                 200                 205

Met Met Ser Lys Lys Lys Gly Gln Lys Trp Gly Gln Glu Lys Val Ser
    210                 215                 220

Phe Pro Gln Lys Thr Asp Ser Leu Gly Ser Asn Lys Glu Tyr Pro Asp
225                 230                 235                 240

Met Met Ser Arg Glu Arg Gln Lys Trp Ile Gln Glu Lys Asp Ser Phe
                245                 250                 255

Ser Gln Lys Asn Asp Ser Leu Ser Ser Asn Lys Glu His Pro Glu Ile
            260                 265                 270

Met Asn Arg Lys Arg Gln Lys Trp Gly Gln Glu Asn Ile Ser Phe Ala
        275                 280                 285

Gln Lys Asn Asp Ser Pro Gly Ser Ser Lys Glu His Pro Asp Met Met
    290                 295                 300

Asn Arg Glu Arg Gln Lys Trp Ser Gln Glu Lys Asn Leu Phe Tyr Gln
305                 310                 315                 320

Lys Asn Asp Ser Leu Gly Ser Asn Lys Glu His Pro Glu Ile Met Asn
                325                 330                 335

Arg Asn Arg Gln Asn Trp Gly Glu Glu Asn Val Ser Phe Ser Gln Lys
            340                 345                 350

Asn Asp Ser Leu Asp Ser Asn Lys Lys His Pro Glu Met Leu Asn Gly
        355                 360                 365

Glu Lys Glu Pro His Phe Asn Gly Ser Ile Asp Phe Asn Thr Leu Pro
    370                 375                 380

Phe Leu Ser Gly Gln Pro Lys Glu Gly Leu Val Ile Ala Tyr Arg Leu
385                 390                 395                 400

Leu Glu Leu Ser Ser Thr Trp Thr Pro Glu Val Ser Ser Tyr Arg Val
                405                 410                 415

Gly Lys Ile Ser Ser Tyr Asn Ser Glu Ala Asn Arg Val Leu Leu Met
            420                 425                 430

Pro Val Ala Glu Phe Pro Val Ile Cys Thr Glu Asp Glu Ser Ser Lys
        435                 440                 445

Gln Pro Asp Ser Ser Ile Tyr Asn Glu Asp Gly Ser Leu Glu Ile Glu
    450                 455                 460

Phe Ser Ala Leu Leu Glu Val Arg Leu Met Asn Ser Thr Pro Asp Gln
465                 470                 475                 480

Gly Val His Glu Gly Val Ile Glu Gly Ser Ala Ala Asn Glu Ser Thr
                485                 490                 495

Pro Val Leu Gly Ser Ser Lys Lys Lys Asn Glu Thr Pro Val Pro Gly
            500                 505                 510

Ala Gly Glu Val Ser Asn Gly Lys Gln Thr Arg Ser Thr Pro Ser Glu
```

```
        515                 520                 525

Asn Gly Gly Val Asn Leu Trp Glu Gln Phe Ser Asp Thr Leu Lys Ser
    530                 535                 540

Lys Lys Ala Glu Leu Ala Gln Glu Ser Asn Trp Asp Lys Ala Ser Thr
545                 550                 555                 560

Gly Lys Ser Pro Trp Ser Tyr Arg Pro Met Arg Gly Thr Ala Leu Gly
                565                 570                 575

Pro Thr Met Ala Phe Leu Arg Ser Gln Lys Lys Ile
            580                 585


<210> SEQ ID NO 11
<211> LENGTH: 306
<212> TYPE: PRT
<213> ORGANISM: Solanum esculentum

<400> SEQUENCE: 11

Met Glu Asn Ser Arg Glu Phe Leu Ser Asn Gly Lys Pro Ala Asp Pro
1               5                   10                  15

Gly Leu Gln Ile Ile Arg His Pro Ser Tyr Gln Ser Cys Gly Lys Leu
            20                  25                  30

Ser Leu Ser Trp Phe Asp Ile Arg Val Phe Tyr Ile Arg Ile Ser Asn
        35                  40                  45

Phe Met Val Asp Asp Ser Thr Pro Glu Ser Leu Thr Leu Asn His Ile
    50                  55                  60

Pro Leu Ser Pro Asp Thr Leu Leu Glu Val Asn Gly Lys Arg Cys Ser
65                  70                  75                  80

Val Tyr Ser Glu Gly Ala Ser Cys Phe Leu Arg Arg Asp Arg Val Asp
                85                  90                  95

Lys Lys Ala Glu Glu Ala Thr Phe Val Ser Thr Asp Ser Ile Arg Leu
            100                 105                 110

Thr Gly Ser Val Asn Phe Glu Val Ser Tyr Lys Asp Asp Leu Phe Leu
        115                 120                 125

Ser Gly Thr Leu Glu Met Ala Asn Ile Asn Asp Ser Gln Asn Cys Leu
    130                 135                 140

Arg Arg Trp Ser Met Asn Cys Glu Ser Val Met Ser Ala Gly Thr Gly
145                 150                 155                 160

Phe Leu Lys Gly Lys His Ile Val Gly Ser Glu Ser Leu Ser Pro Thr
                165                 170                 175

Ile Glu Val Tyr Val Thr Gly Cys Phe Ser Gly Thr Pro Ile Ile Leu
            180                 185                 190

Thr Lys Thr Leu Gln Leu Asn His Arg Lys Lys His His Arg Lys Gly
        195                 200                 205

Met Leu Asp Ser Ile Pro Glu His Asp Thr Ser Glu Gln His Lys Glu
    210                 215                 220

Val Ser Ser Glu His Asp Leu Gln Val Thr Glu Tyr Asn Gly Asn Tyr
225                 230                 235                 240

Lys Pro Glu Ser Glu Glu Asp Tyr Asn Asn Met Tyr Trp Gly Arg Thr
                245                 250                 255

Glu Leu Met Asp Gly Glu Asp Gly Glu Met Ser Trp Phe Asn Ala Gly
            260                 265                 270

Val Arg Val Gly Val Gly Ile Gly Leu Gly Ile Cys Val Gly Val Gly
        275                 280                 285

Val Gly Val Gly Leu Leu Val Arg Thr Thr Arg Asn Leu Arg Arg Arg
    290                 295                 300
```

```
Leu Met
305


<210> SEQ ID NO 12
<211> LENGTH: 306
<212> TYPE: PRT
<213> ORGANISM: Solanum esculentum

<400> SEQUENCE: 12

Met Glu Asn Ser Arg Glu Phe Leu Ser Asn Gly Lys Pro Ala Asp Pro
1               5                   10                  15

Gly Leu Gln Ile Ile Arg His Pro Ser Tyr Gln Ser Cys Gly Lys Leu
            20                  25                  30

Ser Leu Ser Trp Phe Asp Ile Arg Val Phe Tyr Ile Arg Ile Ser Asn
        35                  40                  45

Phe Met Val Asp Asp Ser Thr Pro Glu Ser Leu Thr Leu Asn His Ile
    50                  55                  60

Pro Leu Ser Pro Asp Thr Leu Leu Glu Val Asn Gly Lys Arg Cys Ser
65                  70                  75                  80

Val Tyr Ser Glu Gly Ala Ser Cys Phe Leu Arg Arg Asp Arg Val Asp
                85                  90                  95

Lys Lys Ala Glu Glu Ala Thr Phe Val Ser Thr Asp Ser Ile Arg Leu
            100                 105                 110

Thr Gly Ser Val Asn Phe Glu Val Ser Tyr Lys Asp Asp Leu Phe Leu
        115                 120                 125

Ser Gly Thr Leu Glu Met Ala Asn Ile Asn Asp Ser Gln Asn Cys Leu
    130                 135                 140

Arg Arg Trp Ser Met Asn Cys Glu Ser Val Met Ser Ala Gly Thr Gly
145                 150                 155                 160

Phe Leu Lys Gly Lys His Ile Val Gly Ser Glu Ser Leu Ser Pro Thr
                165                 170                 175

Ile Glu Val Tyr Val Thr Gly Cys Phe Ser Gly Thr Pro Ile Ile Leu
            180                 185                 190

Thr Lys Thr Leu Gln Leu Asn His Arg Lys Lys His His Arg Lys Gly
        195                 200                 205

Met Leu Asp Ser Ile Pro Glu His Asp Thr Ser Glu Gln His Lys Glu
    210                 215                 220

Val Ser Ser Glu His Asp Leu Gln Val Thr Glu Tyr Asn Gly Asn Tyr
225                 230                 235                 240

Lys Pro Glu Ser Glu Glu Asp Tyr Asn Asn Met Tyr Trp Gly Arg Thr
                245                 250                 255

Glu Leu Met Asp Gly Glu Asp Gly Glu Met Ser Trp Phe Asn Ala Gly
            260                 265                 270

Val Arg Val Gly Val Gly Ile Gly Leu Gly Ile Cys Val Gly Val Gly
        275                 280                 285

Val Gly Val Gly Leu Leu Val Arg Thr Thr Arg Asn Leu Arg Arg Arg
    290                 295                 300

Leu Met
305


<210> SEQ ID NO 13
<211> LENGTH: 1260
<212> TYPE: DNA
<213> ORGANISM: Vitis vinifera

<400> SEQUENCE: 13
```

```
ttggatggta cttccaattc catcccctca atcaatgttg ttgaagggtt tcagtgagta     60

ttggtaaagc tcctgaatca tggaatcttc ttatgaggca gtaagaaatg atgaaccagc    120

caatcctggc cttcagatta ttaggtacac cccttaccaa tcctggtcat caccttggtt    180

tgatttgaga gttttttatg tgagaatcag caattttgag gttgatgatt caacccctga    240

atacctcact ctcaatcaca tccccctaag ccctgacacc ctccttgaag tgaatgscac    300

cagaagtagt attttctcag atggagtctc ctccctttg agaagggatc gagtggataa    360

gaagtctgaa gaagccacat ttgtgagcac agacagyata aggttgactg ggagtgtcaa    420

atttgaggtt ttcgataaag aggatctcat tctttcaggt gctttggaga tctccaatag    480

taatggtttt attggggagt cgaagaccaa tgccaagcaa tggagcatga attgtgaatc    540

agaaatcact gcaggaactg ccttcttgaa gggtaaacaa attgttggtt ctgagttacc    600

acctccaacc attgaggtct atgttgcagg ctgtttctca ggaactccaa tcatcttaac    660

caagactttg cagcttagtt ttcggaagaa gcataatagg aagggtgcat tggattctat    720

tcctgagtat gaaacaactg aatgccagaa aatgttccca tcatcgcttg atttgcagat    780

gtctgaatac acaaactaca agcctgaaag tgaagaagac tacatgtayt ggaggagaac    840

agaatttatg gaaggtgaag atggtgaact ctcctggttc aatgctggtg tgagggttgg    900

tgttgggatt ggccttggca tttgtctggg aatcggaata ggagttgggt tgctggtccg    960

tacttatcaa gcaaccaccc gaaacttcaa aagggggctc atgtaattcc yattgtctgc   1020

acaacaactt tctccctcaa atccaaaggc agctgactga cttgtttttg agattgcatc   1080

tttgacaaat ttttacrggc tttgaagtca ccttcgtgta gctaacacag acattgctgt   1140

tcagtaagck ttttgtttga ttttkaagtt tcattgctat tgtggtgttt gtttgtttag   1200

aagggcatga taattgtgaa gctggtagaa gtggaaaggg cttacaaatc cctgaatcga   1260
```

```
<210> SEQ ID NO 14
<211> LENGTH: 308
<212> TYPE: PRT
<213> ORGANISM: Vitis vinifera
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid

<400> SEQUENCE: 14

Met Glu Ser Ser Tyr Glu Ala Val Arg Asn Asp Glu Pro Ala Asn Pro
1               5                   10                  15

Gly Leu Gln Ile Ile Arg Tyr Thr Pro Tyr Gln Ser Trp Ser Ser Pro
            20                  25                  30

Trp Phe Asp Leu Arg Val Phe Tyr Val Arg Ile Ser Asn Phe Glu Val
        35                  40                  45

Asp Asp Ser Thr Pro Glu Tyr Leu Thr Leu Asn His Ile Pro Leu Ser
    50                  55                  60

Pro Asp Thr Leu Leu Glu Val Asn Xaa Thr Arg Ser Ser Ile Phe Ser
65                  70                  75                  80

Asp Gly Val Ser Ser Leu Leu Arg Arg Asp Arg Val Asp Lys Lys Ser
                85                  90                  95
```

-continued

```
Glu Glu Ala Thr Phe Val Ser Thr Asp Xaa Ile Arg Leu Thr Gly Ser
            100                 105                 110

Val Lys Phe Glu Val Phe Asp Lys Glu Asp Leu Ile Leu Ser Gly Ala
        115                 120                 125

Leu Glu Ile Ser Asn Ser Asn Gly Phe Ile Gly Glu Ser Lys Thr Asn
    130                 135                 140

Ala Lys Gln Trp Ser Met Asn Cys Glu Ser Glu Ile Thr Ala Gly Thr
145                 150                 155                 160

Ala Phe Leu Lys Gly Lys Gln Ile Val Gly Ser Glu Leu Pro Pro Pro
                165                 170                 175

Thr Ile Glu Val Tyr Val Ala Gly Cys Phe Ser Gly Thr Pro Ile Ile
            180                 185                 190

Leu Thr Lys Thr Leu Gln Leu Ser Phe Arg Lys Lys His Asn Arg Lys
        195                 200                 205

Gly Ala Leu Asp Ser Ile Pro Glu Tyr Glu Thr Thr Glu Cys Gln Lys
    210                 215                 220

Asn Val Pro Ser Ser Leu Asp Leu Gln Met Ser Glu Tyr Thr Asn Tyr
225                 230                 235                 240

Lys Pro Glu Ser Glu Glu Asp Tyr Met Xaa Trp Arg Arg Thr Glu Phe
                245                 250                 255

Met Glu Gly Glu Asp Gly Glu Leu Ser Trp Phe Asn Ala Gly Val Arg
            260                 265                 270

Val Gly Val Gly Ile Gly Leu Gly Ile Cys Leu Gly Ile Gly Ile Gly
        275                 280                 285

Val Gly Leu Leu Val Arg Thr Tyr Gln Ala Thr Thr Arg Asn Phe Lys
    290                 295                 300

Arg Gly Leu Met
305
```

IDENTIFICATION AND USE OF TOMATO GENES CONTROLLING SALT/DROUGHT TOLERANCE AND FRUIT SWEETNESS

CROSS-REFERENCE TO RELATED APPLICATIONS

This application is a National Stage Entry of International Patent Application No. PCT/US2014/28764, filed on Mar. 14, 2014, which claims priority to U.S. provisional application No. 61/783,288 filed on Mar. 14, 2013, each of which is hereby incorporated by reference in its entirely for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EVOL_005_01WO_SeqList_ST25.txt, date recorded: Mar. 14, 2014, file size 39 kilobytes).

TECHNICAL FIELD

The invention relates to the identification and use of nucleic acid sequences for salt/drought tolerance and fruit sweetness in plants.

BACKGROUND

A major problem of the 21st century will be sufficient food and feed for a growing global population. At the current world population growth rate of about 80 million people per year, food production must increase 20% in developed countries and 60% in developing countries to just keep pace with current food consumption. The rapidly increasing GDPs of China and India are raising the standard of living such that current food consumption levels will become unacceptable to more people and food production will have to be further increased.

Some estimate that 90% of the world's arable land is already cultivated (not counting forests and unsuitable areas), although food yields from agriculture in Africa are far below European, U.S. and even Chinese yields and some arable African land is under exploited. However, about 24 million acres of arable land are abandoned each year due to salinization and other physical/chemical degradations. Food production could be increased if crop productivities can be maintained in spite of land salinization and aridity.

The identification and use of salt/drought tolerance and fruit sweetness are important to plant husbandry and crop production, particularly for commercial crop production in agronomy and horticulture.

Past researchers have used salt-tolerant and salt-sensitive plant models in attempts to find salt and drought tolerance genes. For example, expression profiling studies have identified hundreds of genes that are regulated differently in salt-tolerant vs. salt-sensitive plant species and almost 100 of these genes have been cloned into salt-sensitive model plants and shown to increase salt tolerance. However, to date, none of these efforts have led to the ability to develop salt-tolerant cultivated plant species.

Fruit sugar content is a trait of interest to tomato breeders. Fruit sugar contributes to flavor, so is commercially valuable. Fruit sugar content is three times higher in the Galapagos tomato than the cultivated tomato (Balibrea et al., 2006). This trait has been shown to vary in other wild tomato species as well (Fridman el al., 2000). A single QTL accounts for most of the variation in this trait between cultivated tomato and *S. pennellii* (Fridman et al., 2000), suggesting that a single gene may explain a substantial part of differences in fruit sugar content.

The present invention provides for the identification, characterization and use of tomato genes that control salinity tolerance, drought tolerance and fruit sugar content (i.e., fruit sweetness).

SUMMARY OF THE INVENTION

One goal of the present invention was to identify natural genes in food, feed, and biofuel sources that can be used to significantly increase yields, improve plant health and adaptability, improve product preference and quality, and decrease costs. This was accomplished by applying a cost-effective and rapid approach in order to identify crop plant genes controlling salinity tolerance and drought tolerance that have utility for developing crop plants able to withstand saline and arid conditions; and, by identifying genes controlling sugar content of fruit. The present invention provides the identification and use of genes that have undergone adaptive evolution between two species of tomato: modern cultivated tomato (*Solanum esculentum*) and the more drought- and salt-resistant Galapagos tomato (*Solanum cheesmanni* aka *Solanum cheesmannii; Solanum cheesmaniae; Lycopersicon cheesmanii*).

The present invention provides the identification and use of EGTom1 and/or EGTom2, homologs of EGTom1 and/or EGTom2, orthologs of EGTom1 and/or EGTom2, paralogs of EGTom1 and/or EGTom2, and fragments and variations thereof for altering, e.g. conferring or increasing, salt tolerance, drought tolerance and/or sugar content of fruit (sweetness). Importantly, increased salt tolerance, drought tolerance and/or sugar content of fruit (sweetness) can be obtained using conventional plant breeding methods, whereby such methods optionally also include using any of various biotechnological methods for verifying that the desired EGTom1 and/or EGTom2, homologs of EGTom1 and/or EGTom2, orthologs of EGTom1 and/or EGTom2, paralogs of EGTom1 and/or EGTom2, and fragments and variations thereof are present in the resulting crosses and offspring.

In some embodiments, the present invention provides isolated nucleic acid sequences coding for EGTom1 (SEQ ID NO: 1) and/or EGTom2 (SEQ ID NO: 2), homologs of EGTom1 and/or EGTom2, orthologs of EGTom1 (e.g., SEQ ID Nos: 3 and 4) and/or EGTom2 (e.g., SEQ ID Nos: 5 and 6), paralogs of EGTom1 and/or EGTom2, and fragments and variations thereof. The present invention also provides chimeric genes, constructs, recombinant DNA, vectors, plant cells, plant tissues, plant parts, plant tissue cultures and/or whole plants comprising such nucleic acid sequences.

In one embodiment, the present invention provides polynucleotides for altering and/or increasing salt tolerance, drought tolerance and/or sugar content of fruit (sweetness) comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to nucleic acids coding for EGTom1 and/or EGTom2, homologs of EGTom1 and/or EGTom2, orthologs of EGTom1 and/or EGTom2, paralogs of EGTom1 and/or EGTom2, and fragments and variations thereof.

The present invention further provides isolated amino acid sequences (e.g., a peptide, polypeptide and the like) comprising an amino acid sequence encoded by the nucleic acid sequences for EGTom1 and/or EGTom2, homologs of EGTom1 and/or EGTom2, orthologs of EGTom1 and/or EGTom2, paralogs of EGTom1 and/or EGTom2, and fragments and variations thereof.

In some embodiments, the present invention provides isolated amino acid sequences which form a protein that shares an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to an amino acid sequence encoded by the nucleic acid sequences for EGTom1 and/or EGTom2, homologs of EGTom1 and/or EGTom2, orthologs of EGTom1 and/or EGTom2, paralogs of EGTom1 and/or EGTom2, and fragments and variations thereof.

In one embodiment, the present invention provides isolated amino acid sequences which encode a protein that shares an amino acid having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to an amino acid sequence encoded by the polypeptide sequences for EGTom1 and/or EGTom2, homologs of EGTom1 and/or EGTom2, orthologs of EGTom1 and/or EGTom2, paralogs of EGTom1 and/or EGTom2, and fragments and variations thereof.

The present invention also provides a chimeric gene comprising the isolated nucleic acid sequence of any one of the polynucleotides described above operably linked to suitable regulatory sequences.

The present invention also provides a recombinant construct comprising the chimeric genes as described above.

The present invention further comprises interfering RNA (RNAi) based on the expression of the nucleic acid sequences of the present invention, wherein such RNAi includes but is not limited to microRNA (miRNA) and small interfering RNA (siRNA) which can be used in gene silencing constructs.

The present invention also provides transformed host cells comprising the chimeric genes as described above. In one embodiment, said host cells are selected from the group consisting of bacteria, yeasts, filamentous fungi, algae, animals, and plants.

The present invention in another aspect provides plants comprising in its genome one or more genes as described herein, one or more genes with mutations as described herein, or the chimeric genes as described herein.

The present invention in another aspect provides plant seed obtained from the plants described herein, wherein the plants producing such seeds comprise in their genomes one or more genes as described herein, one or more genes with mutations as described herein, or the chimeric genes as described herein.

In some embodiments, the methods comprise introducing mutations in one or more nucleic acid sequences for EGTom1 and/or EGTom2, homologs of EGTom1 and/or EGTom2, orthologs of EGTom1 and/or EGTom2, paralogs of EGTom1 and/or EGTom2, and fragments and variations thereof.

In one aspect, the present invention provides methods of breeding plants to alter, e.g. confer or increase, salt tolerance, drought tolerance and/or sugar content of fruit (sweetness) when compared to the parent plant without the polynucleotides of the present invention (i.e., a non-transgenic plant for the gene of interest), a wildtype plant or an appropriate check plant. In one embodiment, such methods comprise making a cross between a plant comprising one or more nucleic acid sequences for EGTom1 and/or EGTom2, homologs of EGTom1 and/or EGTom2, orthologs of EGTom1 and/or EGTom2, paralogs of EGTom1 and/or EGTom2, and fragments and variations with a second plant of the same or different species to produce an F1 plant; backcrossing the F1 plant to the second plant; and repeating the backcrossing step to generate a near isogenic line, wherein the one or more nucleic acid sequences for EGTom1 and/or EGTom2, homologs of EGTom1 and/or EGTom2, orthologs of EGTom1 and/or EGTom2, paralogs of EGTom1 and/or EGTom2, and fragments and variations thereof are integrated into the genome of the second plant; wherein the near isogenic line derived from the second plant has altered, e.g. increased, salt tolerance, drought tolerance and/or sugar content of fruit (sweetness) when compared to the parent plant without the nucleic acids of the present invention (i.e., non-transgenic plant), a wildtype plant or an appropriate check plant. Optionally, such methods can be facilitated by using various biotechnological methods to verify that the nucleic acid sequences for EGTom1 and/or EGTom2, homologs of EGTom1 and/or EGTom2, orthologs of EGTom1 and/or EGTom2, paralogs of EGTom1 and/or EGTom2, and fragments and variations thereof are included in the second plant.

The present invention provides isolated, recombinant, or synthetic polynucleotides comprising a nucleic acid sequence selected from the following: (a) a nucleic acid sequence having at least 95% identical nucleotides to a nucleic acid sequence coding for EGTom1 (SEQ ID NO: 1) and/or EGTom2 (SEQ ID NO: 2); (b) a nucleic acid sequence having at least 95% identical nucleotides to a nucleic acid sequence coding for a homolog of EGTom1 and/or EGTom2; (c) a nucleic acid sequence having at least 95% identical nucleotides to a nucleic acid sequence coding for an ortholog of EGTom1 and/or EGTom2; (d) a nucleic acid sequence having at least 95% identical nucleotides to a nucleic acid sequence coding for a paralog of EGTom1 and/or EGTom2; (e) complements of a nucleic acid sequence of (a), (b), (c) or (d); (f) reverse complements of a nucleic acid sequence of (a), (b), (c) or (d); (g) reverse sequences of a nucleic acid sequence of (a), (b), (c) or (d); and, (h) fragments and variations of a nucleic acid sequence of (a), (b), (c), (d), (e), (f) and (g).

The present invention provides vectors comprising said isolated, recombinant, or synthetic polynucleotides. The present invention provides genetic constructs comprising said isolated, recombinant, or synthetic polynucleotides. The present invention further provides genetic constructs comprising, in the 5'-3' direction: (a) a promoter sequence, (b) said isolated, recombinant, or synthetic polynucleotides; and (c) a gene termination sequence. In some embodiments such genetic constructs include said isolated, recombinant, or synthetic polynucleotides having an open reading frame encoding a polypeptide capable of altering salt tolerance, drought tolerance and/or sugar content of fruit (sweetness).

The present invention also provides transgenic cells comprising the genetic constructs of the present invention.

The present invention further provides organisms comprising the transgenic cells of the present invention. In some embodiments, the present invention provides plants comprising a transgenic cell of the present invention, or a part or propagule or progeny thereof.

The present invention also provides progeny plants of the plant of the present invention, wherein the progeny plants have an altered salt tolerance, drought tolerance and/or sugar content of fruit (sweetness) as a result of inheriting the polynucleotide when compared to the wildtype plant or an appropriate check plant.

The present invention provides methods of producing hybrid seed comprising crossing the plants or progeny plants of the present invention with a different plant of the same species, and harvesting the resultant seed.

The present invention provides methods for modifying gene expression in a target organism comprising stably incorporating into the genome of the organism a genetic construct according to the present invention. In some embodiments, the target organism is a plant. In some embodiments, the plant is a cultivated tomato plant (*Solanum esculentum*).

The present invention provides methods for producing a plant having altered salt tolerance, drought tolerance and/or sugar content of fruit (sweetness) comprising: (a) transforming a plant cell with a genetic construct to provide a transgenic cell, wherein the genetic construct comprises: (i) a promoter sequence; (ii) an isolated, recombinant, or synthetic polynucleotide sequence of the present invention; and (c) a gene termination sequence; and (b) cultivating the transgenic cell under conditions conducive to regeneration and mature plant growth of a plant having altered salt tolerance, drought tolerance and/or sugar content of fruit (sweetness) when compared to the parent plant without the genetic construct of the present invention (i.e., non-transgenic plant), a wildtype plant or an appropriate check plant.

The present invention provides methods for modifying a phenotype of a target organism, comprising stably incorporating into the genome of the target organism a genetic construct comprising: (a) a promoter sequence; (b) an isolated, recombinant, or synthetic polynucleotide sequence of the present invention; and (c) a gene termination sequence. Such methods include wherein the target organism is a plant.

The present invention also presents processes of determining the presence or absence of a polynucleotide coding for EGTom1 (SEQ ID NO: 1) and/or EGTom2 (SEQ ID NO: 2), homologs of EGTom1 and/or EGTom2, orthologs of EGTom1 (e.g., SEQ ID Nos: 3 and 4) and/or EGTom2 (e.g., SEQ ID Nos: 5 and 6), paralogs of EGTom1 and/or EGTom2, and fragments and variations thereof in a plant, wherein the process comprises at least one of:

(a) isolating nucleic acid molecules from said plant and amplifying sequences homologous to the polynucleotide;

(b) isolating nucleic acid molecules from said plant and performing a Southern hybridization to detect the polynucleotide;

(c) isolating proteins from said plant and performing a Western Blot using antibodies to a protein encoded by the polynucleotide; and/or (d) demonstrating the presence of mRNA sequences derived from a polynucleotide mRNA transcript and unique to the polynucleotide.

The present invention also provides methods of breeding plants to produce altered salt tolerance, drought tolerance and/or sugar content of fruit (sweetness) when compared to the parent plant without the nucleic acids or genes of the present invention (i.e., non-transgenic plant), a wildtype plant or an appropriate check plant, said methods comprising:

i) making a cross between a plant with an isolated, recombinant, or synthetic polynucleotide sequence of the present invention with a second plant to produce a F1 plant:

ii) backcrossing the F1 plant to the second plant; and iii) repeating the backcrossing step to generate a near isogenic or isogenic line, wherein the isolated, recombinant, or synthetic polynucleotide sequence of the present invention is integrated into the genome of the second plant and the near isogenic or isogenic line derived from the second plant with the isolated, recombinant, or synthetic polynucleotide sequence has altered salt tolerance, drought tolerance and/or sugar content of fruit (sweetness) compared to that of the second plant without the isolated, recombinant, or synthetic polynucleotide sequence. The present invention includes such processes wherein the plant is cultivated tomato (*Solanum esculentum*).

The present invention also provides methods of producing a plant with altered salt tolerance, drought tolerance and/or sugar content of fruit (sweetness), the process comprising:

(b) crossing a first plant containing a polynucleotide coding for EGTom1 (SEQ ID NO: 1) and/or EGTom2 (SEQ ID NO: 2), homologs of EGTom1 and/or EGTom2, orthologs of EGTom1 (e.g., SEQ ID Nos: 3 and 4) and/or EGTom2 (e.g., SEQ ID Nos: 5 and 6), paralogs of EGTom1 and/or EGTom2, and fragments and variations thereof to a second plant, and harvesting the resultant seed;

(b) determining the presence of the polynucleotide in the resultant seed or in cells or tissues of a plant grown from the resultant seed; wherein the determining comprises at least one of:

(i) isolating nucleic acid molecules from the resultant seed or in cells or tissues of a plant grown from the resultant seed and amplifying sequences homologous to the polynucleotide;

(ii) isolating nucleic acid molecules from the resultant seed or in cells or tissues of a plant grown from the resultant seed and performing a Southern hybridization to detect the polynucleotide;

(iii) isolating proteins from the resultant seed or in cells or tissues of a plant grown from the resultant seed and performing a Western Blot using antibodies to a protein encoded by the polynucleotide; and/or (iv) demonstrating the presence in the resultant seed or in cells or tissues of a plant grown from the resultant seed of mRNA sequences derived from a polynucleotide mRNA transcript and unique to the polynucleotide.

The present invention also provides for such methods further comprising confirming that the resultant seed or the cells or tissues of the plant grown from the resultant seed contain the polynucleotide. In some embodiments such methods further include using the resultant plant containing the polynucleotide in a plant breeding scheme. In some embodiments such methods further include crossing the resultant plant containing the polynucleotide with another plant of the same species.

The present invention also provides isolated, recombinant, or synthetic polypeptides, wherein the polypeptide comprises an amino acid sequence having at least 90% identity to a polypeptide encoded by an EGTom1 (SEQ ID NO: 1) and/or EGTom2 (SEQ ID NO: 2), wherein the isolated, recombinant, or synthetic polypeptide when expressed in a plant species alters salt tolerance, drought tolerance and/or sugar content of fruit (sweetness).

The present invention also provides for the use of any of the isolated, recombinant, or synthetic polynucleotides of the present invention; and, the use of any of the isolated, recombinant, or synthetic polypeptides of the present invention.

The present invention provides the genetic constructs of the present invention which include a promoter sequence that is heterologous to the isolated, recombinant, or synthetic polynucleotides of EGTom1 and/or EGTom2.

The present invention also provides transgenic cells, organisms, and plants, progeny plants of the present invention for which the isolated, recombinant, or synthetic polynucleotide is heterologous to the transgenic cell.

In some embodiments, the present invention teaches a transgenic tomato or grape plant, plant part, plant cell, or plant tissue culture comprising a construct, comprising a nucleic acid encoding an EGTom polypeptide having 95% sequence identity to any one of SEQ ID NOs 8, 7, 9-12, or 14; wherein said transgenic tomato or grape plant, or transgenic tomato or grape plant produced from said plant part, plant cell, or plant tissue culture, expresses said EGTom polypeptide, and has increased fruit sweetness or increased salt or drought tolerance compared to an untransformed control tomato or grape plant.

In some embodiments, the nucleic acid comprised in the construct of the present invention encodes an EGTom polypeptide having 96% sequence identity to any one of SEQ ID NOs 7-12, or 14.

In some embodiments, the nucleic acid comprised in the construct of the present invention encodes an EGTom polypeptide having 97% sequence identity to any one of SEQ ID NOs 7-12, or 14.

In some embodiments, the nucleic acid comprised in the construct of the present invention encodes an EGTom polypeptide having 98% sequence identity to any one of SEQ ID NOs 7-12, or 14.

In some embodiments, the nucleic acid comprised in the construct of the present invention encodes an EGTom polypeptide having 99% sequence identity to any one of SEQ ID NOs 7-12, or 14.

In some embodiments the transgenic tomato plant, plant part, plant cell, or plant tissue culture of the present invention comprises a nucleic acid encoding an EGTom polypeptide having 95% sequence identity to SEQ ID NO 8.

In some embodiments the transgenic grape plant, plant part, plant cell, or plant tissue culture of the present invention comprises a nucleic acid encoding an EGTom polypeptide having 95% sequence identity to SEQ ID NO 14.

In some embodiments, the transgenic tomato or grape plant, plant part, plant cell, or plant tissue culture of the present invention comprises a construct further comprising a gene termination sequence.

In some embodiments, the transgenic tomato or grape plant, plant part, plant cell, or plant tissue culture of the present invention comprises a construct further comprising a promoter.

In some embodiments, the construct of the transgenic tomato or grape plant, plant part, plant cell, or plant tissue culture, of the present invention is an overexpression construct.

In some embodiments, the present invention teaches a genetic construct comprising, in the 5'-3' direction: (i) a promoter sequence; (ii) the nucleic acid sequence of the present invention; and (iii) a gene termination sequence; wherein expression of said genetic construct in a plant causes the plant to bear fruit with increased sweetness, or enhances the salt/drought tolerance of the plant compared to an untransformed plant.

In some embodiments, the present invention teaches a method for producing a transgenic tomato or grape plant with increased fruit sweetness or increased drought or salt tolerance, said method comprising: (i) transforming a tomato plant cell with a construct comprising a nucleic acid sequence encoding a EGTom polypeptide having at least 95% identity to any one of SEQ ID NOs 7-12, or 14; and (ii) cultivating the transgenic tomato or grape cell under conditions conducive to regeneration and mature plant growth;

wherein the transgenic tomato or grape plant regenerated from said transgenic tomato or grape plant cell expresses said EGTom polypeptide, and has increased fruit sweetness, or increased drought or salt tolerance compared to untransformed control tomato or grape plants.

In some embodiments, the present invention teaches methods of producing transgenic tomato or grape plants in which the construct is an over expression construct.

In some embodiments, the present invention teaches a method of producing hybrid tomato or grape seed, said method comprising: crossing the transgenic tomato plant of the present invention with another tomato or grape plant, and harvesting the resultant seed.

In some embodiments, the present invention teaches a method of breeding tomato or grape plants to produce plants with increased fruit sweetness or increased drought or salt tolerance, said method comprising: (i) making a cross between a first transgenic tomato or grape plant of the present invention with a second tomato or grape plant to produce an F1 plant; (ii) backcrossing the F1 plant to the second tomato or grape plant; and (iii) repeating the backcrossing step one or more times to generate a near isogenic or isogenic line, wherein the construct of the present invention is integrated into the genome of the second plant and the near isogenic or isogenic line derived from the second tomato or grape plant with the nucleic acid encoding the EGTom polypeptide has increased fruit sweetness or increased drought or salt tolerance compared to a tomato or grape second plant without said nucleic acid sequence.

In some embodiments, the present invention teaches a method of culturing plant tissue, said method comprising culturing at least part of the plant produced by any of the transformation or breeding methods of the present invention, wherein said plant is cultured in conditions conducive to plant regeneration, thereby regenerating said plant.

In some embodiments of the present invention, progeny plants produced by the transformation, breeding, or tissue culture methods of the present invention, wherein the progeny plants have increased fruit sweetness or increased drought or salt tolerance as a result of inheriting the polynucleotide when compared to a parent plant without the genetic construct of the present invention (i.e., non-transgenic plant), a wildtype plant or an appropriate check plant.

In some embodiments the transgenic tomato plant of the present invention is a cultivated tomato plant (*Solanum esculentum*).

In some embodiments, the present invention teaches a method of growing a plant comprising placing the seeds from the plants of the present invention an environment conducive to plant growth, thereby growing the plant.

BRIEF DESCRIPTION OF THE DRAWINGS

FIG. 1 a bar graph of Brix sweetness values (y-axis) for tomato plants (x-axis) transformed with EGTom2 of SEQ ID No 2. Brackets indicate expression level of transgene. Brix values increase in a dose dependent manner.

DETAILED DESCRIPTION

Definitions

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom), including but not limited to, *Glycine* spp. (e.g., soybean), *Solanaceae* species (e.g., *Solanum lycopersicum, Solanum chemielewskii, Solanum esculentum, Solanum cheesmaniae, Solanum habrochaites. Solanum corneliomulleri, Capsicum annuum, Solanum melongena, Solanum tuberosum*), *Phaseolus vulgaris, Coffee arabica, Zea mays, Sorghum* spp., *Oryza sativa, Triticum* spp. *Hordeum* spp., *Gossypium hirsutum, Heliotropium curassavicum* and *Vigna unguiculata.*

As used herein, the term "plant part" refers to any part of a plant including but not limited to the shoot, root, stem, seeds, fruits, stipules, leaves, petals, flowers, ovules, bracts, branches, petioles, internodes, bark, pubescence, tillers, rhizomes, fronds, blades, pollen, stamen, rootstock, scion and the like. The two main parts of plants grown in some sort of media, such as soil, are often referred to as the "above-ground" part, also often referred to as the "shoots", and the "below-ground" part, also often referred to as the "roots".

As used herein when discussing plants, the term "ovule" refers to the female gametophyte, whereas the term "pollen" means the male gametophyte.

As used herein when discussing plants, the term "fruit" refers to the sweet and fleshy product of a tree or other plant (e.g., a tomato plant) that contains seed and can be eaten as food.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "nucleotide change" or "nucleotide modification" refers to, e.g., nucleotide substitution, deletion, and/or insertion, as is well understood in the art. For example, such nucleotide changes/modifications include mutations containing alterations that produce silent substitutions, additions, or deletions, but do not alter the properties or activities of the encoded protein or how the proteins are made. As another example, such nucleotide changes/modifications include mutations containing alterations that produce replacement substitutions, additions, or deletions, that alter the properties or activities of the encoded protein or how the proteins are made.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "protein modification" refers to, e.g., amino acid substitution, amino acid modification, deletion, and/or insertion, as is well understood in the art.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "pathogen" refers to an agent that causes disease, especially a living microorganism such as an insect, a bacterium, virus, nematode or fungus.

As used herein, the term "resistant", or "resistance", describes a plant, line or cultivar that shows fewer or reduced symptoms to a pest, pathogen or to an abiotic stress (e.g., exposure to salt or drought) than a susceptible (or more susceptible) plant, line or variety to that pest, pathogen or abiotic stress. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced compared to uninfected plants.

As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest, pathogen or abiotic stress can depend on the analytical method employed. Resistance is defined by the ISF as the ability of plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance are well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 1 being the resistance score applied to the most resistant plants (e.g., no symptoms, or with the least symptoms), and 5 the score applied to the plants with the most severe symptoms, then a line is rated as being resistant when at least 75% of the plants have a resistance score at a 1, 2, or 3 level, while susceptible lines are those having more than 25% of the plants scoring at a 4 or 5 level. If a more detailed visual evaluation is possible, then one can use a scale from 1 to 10 so as to broaden out the range of scores and thereby hopefully provide a greater scoring spread among the plants being evaluated.

In addition to such visual evaluations, disease evaluations can be performed by determining the pathogen bio-density in a plant or plant part using electron microscopy and/or through molecular biological methods, such as protein hybridization (e.g., ELISA, measuring pathogen protein density) and/or nucleic acid hybridization (e.g., RT-PCR, measuring pathogen RNA density). Depending on the particular pathogen/plant combination, a plant may be determined resistant to the pathogen, for example, if it has a pathogen RNA/DNA and/or protein density that is about 50%, or about 40%, or about 30%, or about 20%, or about 10%, or about 5%, or about 2%, or about 1%, or about 0.1%, or about 0.01%, or about 0.001%, or about 0.0001% of the RNA/DNA and/or protein density in a susceptible plant.

Methods used in breeding plants for disease and abiotic stress resistance are similar to those used in breeding for other characters. It is necessary to know as much as possible about the nature of inheritance of the resistant characters in the host plant and the existence of physiological races or strains of the pathogen.

As used herein, the term "full resistance" is referred to as complete failure of the pathogen to develop after infection, and may either be the result of failure of the pathogen to enter the cell (no initial infection) or may be the result of failure of the pathogen to multiply in the cell and infect subsequent cells (no subliminal infection, no spread). The presence of full resistance may be determined by establishing the absence of pathogen protein or pathogen RNA in cells of the plant, as well as the absence of any disease symptoms in said plant, upon exposure of said plant to an infective dosage of pathogen (i.e. after 'infection'). Among breeders, this phenotype is often referred to as "immune". "Immunity" as used herein thus refers to a form of resistance characterized by absence of pathogen replication even when the pathogen is actively transferred into cells by e.g. electroporation.

As used herein, the term "partial resistance" is referred to as reduced multiplication of the pathogen in the cell, as reduced (systemic) movement of the pathogen, and/or as reduced symptom development after infection. The presence of partial resistance may be determined by establishing the systemic presence of low concentration of pathogen protein or pathogen RNA in the plant and the presence of decreased or delayed disease-symptoms in said plant upon exposure of said plant to an infective dosage of pathogen. Protein concentration may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "tolerant" is used herein to indicate a phenotype of a plant wherein disease-symptoms or abiotic stress-symptoms remain absent upon exposure of said plant to an infective dosage of pathogen, whereby the presence of a systemic or local pathogen infection, pathogen multiplication, at least the presence of pathogen genomic sequences in cells of said plant and/or genomic integration thereof can be established. Tolerant plants are therefore resistant for symptom expression but symptomless carriers of the pathogen. Sometimes, pathogen sequences may be present or even multiply in plants without causing disease symptoms. This phenomenon is also known as "latent infection". In latent infections, the pathogen may exist in a truly latent non-infectious occult form, possibly as an integrated genome or an episomal agent (so that pathogen protein cannot be found in the cytoplasm, while PCR protocols may indicate the present of pathogen nucleic acid sequences) or as an infectious and continuously replicating agent. A reactivated pathogen may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the pathogen or abiotic stress (e.g., high salt levels or drought exposure). In the case of a pathogen, this results in entry of the pathogen into the plant and multiplication and systemic spread of the pathogen, resulting in disease symptoms. The term "susceptible" is therefore equivalent to "non-resistant".

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's. F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon," "dicot" and "dicotyledonous" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "monocotyledon," "monocot" or "monocotyledonous" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present invention relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (plural: "loci") refers to any site that has been defined genetically. A locus may be a gene, or part of a gene, or a DNA sequence that has some regulatory role, and may be occupied by different sequences.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled in molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 Nov. 11; 23(21): 4407-4414).

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "homologous" or "homolog" is known in the art and refers to related sequences that share a common ancestor or family member and are determined based on the degree of sequence identity. The terms "homology", "homologous", "substantially similar" and "corresponding substantially" are used interchangeably herein. Homologs usually control, mediate, or influence the same or similar biochemical pathways, yet particular homologs may give rise to differing phenotypes. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared.

The term "homolog" is sometimes used to apply to the relationship between genes separated by the event of speciation (see "ortholog") or to the relationship between genes separated by the event of genetic duplication (see "paralog").

The term "ortholog" refers to genes in different species that evolved from a common ancestral gene by speciation. Normally, orthologs retain the same function in the course of evolution. Identification of orthologs is critical for reliable prediction of gene function in newly sequenced genomes.

The term "paralog" refers to genes related by duplication within a genome. While orthologs generally retain the same function in the course of evolution, paralogs can evolve new functions, even if these are related to the original one.

"Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80/o, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.).

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "mass selection" refers to a form of selection in which individual plants are selected and the next generation propagated from the aggregate of their seeds. More details of mass selection are described herein in the specification.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "self-crossing", "self pollinated" or "self-pollination" means the pollen of one flower on one plant is applied (artificially or naturally) to the ovule (stigma) of the same or a different flower on the same plant.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "suppression" or "disruption" of regulation refers to reduced activity of regulatory proteins, and such reduced activity can be achieved by a variety of mechanisms including antisense, mutation knockout or RNAi. Antisense RNA will reduce the level of expressed protein resulting in reduced protein activity as compared to wild type activity levels. A mutation in the gene encoding a protein may reduce the level of expressed protein and/or interfere with the function of expressed protein to cause reduced protein activity.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, "regulatory sequences" may include, but are not limited to, promoters, translation leader sequences, introns, and polyadenylation recognition sequences.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

As used herein, the "3' non-coding sequences" or "3' UTR (untranslated region) sequence" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

As used herein, the term "vector". "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, recombinant plant viruses. Non-limiting examples of plant viruses include, TMV-mediated (transient) transfection into tobacco (Tuipe, T-H et al (1993), J. Virology Meth, 42: 227-239), ssDNA genomes viruses (e.g., family Geminiviridae), reverse transcribing viruses (e.g., families Caulimoviridae, Pseudoviridae, and Metaviridae), dsNRA viruses (e.g., families Reoviridae and Partitiviridae), (−) ssRNA viruses (e.g., families Rhabdoviridae and Bunyaviridae), (+) ssRNA viruses (e.g., families Bromoviridae, Closteroviridae, Comoviridae, Luteoviridae, Potyviridae, Sequiviridae and Tombusviridae) and viroids (e.g., families Pospiviroldae and Avsunviroidae). Detailed classification information of plant viruses can be found in Fauquet et al (2008, "Geminivirus strain demarcation and nomenclature". *Archives of Virology* 153:783-821, incorporated herein by reference in its entirety), and Khan et al. (Plant viruses as molecular pathogens; Publisher Routledge, 2002, ISBN 1560228954, 9781560228950). Examples of non-viral vectors include, but are not limited to, liposomes, polyamine derivatives of DNA, and the like.

Various measures are used to assess and describe different aspects of sweetness, but few are as popular as the measurement of soluble solid content (SSC, or Brix; Bumgarner and Matthew Kleinhenz 2012 "Using Brix as an indicator of Vegetable Quality: Instructions for measuring Brix in Cucumber, Leafy Greens, Sweet Corn. Tomato and Watermelon" H&CS department OSU HYG-1653-12).

Brix measurements can be conducted in a variety of ways including through the use of hydrometers in combination with Brix specific gravity tables. In other embodiments the sweetness of tomatoes or other fruits can be determined via techniques well known to those in the art including spectral analysis using refractometers measuring the amount of light refracted from a liquid or with visible/near infrared diffuse transmittance techniques such as in U.S. Pat. No. 5,324,945 (Bumgarner and Matthew Kleinhenz 2012, OSU; and Haiqing et al., 2007 "Measurement of soluble solids content in watermelon by Vis/NIR diffuse transmittance technique" J of Zhejiang Univ Sci B 8(2):105-110).

The present invention provides an isolated nucleic acid sequence comprising a sequence selected from the group consisting of EGTom1 (SEQ ID NO: 1) and/or EGTom2 (SEQ ID NO: 2), homologs of EGTom1 and/or EGTom2, orthologs of EGTom1 (SEQ ID Nos: 3 and 4) and/or EGTom2 (SEQ ID Nos: 5 and 6), paralogs of EGTom1 and/or EGTom2, and fragments and variations thereof. In one embodiment, the present invention provides an isolated polynucleotide encoding the protein produced by the nucleic acid sequence for EGTom1 and/or EGTom2, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to EGTom1 and/or EGTom2.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:237-44, 1988); Higgins and Sharp (*CABIOS,* 5:151-53, 1989); Corpet et al. (*Nuc. Acids Res.,* 16:10881-90, 1988); Huang et al. (*Comp. Appls Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The present invention also provides a chimeric gene comprising the isolated nucleic acid sequence of any one of the polynucleotides described above operably linked to suitable regulatory sequences.

The present invention also provides a recombinant construct comprising the chimeric gene as described above. In one embodiment, said recombinant construct is a gene silencing construct, such as used in RNAi gene silencing.

The expression vectors of the present invention will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present invention also provides a transformed host cell comprising the chimeric gene as described above. In one embodiment, said host cell is selected from the group consisting of bacteria, yeasts, filamentous fungi, algae, animals, and plants.

These sequences allow the design of gene-specific primers and probes for EGTom1 and/or EGTom2, homologs of EGTom1 and/or EGTom2, orthologs of EGTom1 and/or EGTom2, paralogs of EGTom1 and/or EGTom2, and fragments and variations thereof.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

A probe comprises an identifiable, isolated nucleic acid that recognizes a target nucleic acid sequence. A probe includes a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (ed.), *Molecular Cloning: A Laboratory Manual,* 2$^{nd}$ ed., vol. 1-3, Cold Spring Harbor Laboratory Press, Cold Spring Harbor, N.Y., 1989 and Ausubel et al. *Short Protocols in Molecular Biology,* 4$^{th}$ ed., John Wiley & Sons, Inc., 1999.

Methods for preparing and using nucleic acid probes and primers are described, for example, in Sambrook et al. (ed.), *Molecular Cloning: A Laboratory Manual,* 2$^{nd}$ ed., vol. 1-3, Cold Spring Harbor Laboratory Press, Cold Spring Harbor, N.Y., 1989; Ausubel et al. *Short Protocols in Molecular Biology,* 4$^{th}$ ed., John Wiley & Sons, Inc., 1999; and Innis et al. *PCR Protocols, A Guide to Methods and Applications,* Academic Press, Inc., San Diego, Calif., 1990. Amplification primer pairs can be derived from a known sequence, for example, by using computer programs intended for that purpose such as PRIMER (Version 0.5, 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

Salt Tolerance in Plants

Salinization is an adverse result of irrigation (Tanji, 1990). Salts come from primary minerals in soil. All surface and ground waters contain dissolved salts picked up from soil and geologic materials that the water has come in contact with. Water used for irrigation leaves salts behind when it evaporates or is transpired by agricultural plants. The accumulating salts can negatively impact all stages of plant growth, from seed germination through seed set. Yet, irrigation is necessary to attain higher agricultural productivities to meet the growing demand for food and feed.

The need for salt and drought tolerant crops is steadily increasing, as fresh water supplies diminish, irrigation increases, and salinization threatens ever greater acres across the world. The present invention provides the discovery of novel salt and drought resistance genes, using a method that we have previously shown to be successful for yield gene identification in the grass-derived crops (i.e., rice, corn, barley).

Soil salt can decrease osmotic potential of the soil solution, creating water stress in plants (Sairam and Tyagi (2004). Thus it is not surprising that salt-stress and drought-stress appear to elicit similar plant responses, including altered regulation of genes and pathways. Sairam and Tyagi (2004) and Munns and Tester (2008) published detailed reviews of salt tolerance in plants. The studies summarized implicate over one hundred genes that are induced and even more that are repressed when various plants are subjected to salt stress. They describe important cell signalling genes and salt-tolerance pathways such as those for producing osmolytes, polyamines, antioxidants, and ion transport membrane proteins. Cloned genes from these studies have been introduced into model plants resulting in increased halotolerance in the recipient plants. However, despite numerous studies with model systems, only moderate salt tolerant cultivated varieties have been developed [primarily by the Central Soil Salinity Research Institute (CSSRI), Karnal, India]. It has been difficult to develop cultivated varieties that are highly salt stress resistant. With so many genes implicated in salt and drought tolerance, it has been difficult to narrow in on the key genes with large impacts that control or influence the activity of many other genes.

*Solanum*

Worldwide, the most valuable vegetable crop is the cultivated tomato (*Solanum esculentum*) (Bai and Lindhout, 2007). The tomato was domesticated in the New World, likely some 8-9,000 years ago. The exact locale of this domestication is uncertain (Paran and van der Knaap, 2007): evidence points to either South America (Peralta and Spooner, 2007; Paran and van der Knaap, 2007; Bai and Lindhout, 2007), where potatoes (Spooner et al., 2005) were also domesticated, or, less likely, to Mexico (Peralta and Spooner, 2007; Paran and van der Knaap, 2007; Bai and Lindhout, 2007), where maize (Piperno and Flannery 2001; Matsuoka et al., 2002) was domesticated, at about the same time. Even today, the center of genetic diversity for wild tomato species lies in the Andes (Nuez el al., 2004; Paran and van der Knaap, 2007).

The exact ancestor to cultivated tomato is unclear (Nesbitt and Tanksley, 2002; Paran and van der Knaap, 2007; Bai and Lindhout, 2007), but is generally thought to be one of the fourteen or so species of the genus *Solanum* that can be found growing wild, mostly in small isolated populations in the Andes. A (perhaps) feral form of the cultivated tomato (*S. esculentum* var. *cerasiforme*) is most often mooted as the putative ancestor (Nesbitt and Tanksley, 2002).

The complex of wild tomato in western South America (and Galapagos) has long been considered to constitute a separate genus, *Lycopersicon*, but recent phylogenetic work confirms that this clade is nested within *Solanum*, and most recent literature assigns the tomatoes to the genus *Solanum*: we follow that assignment here. As with the particular progenitor species to the cultivated tomato, the number of wild tomato species is uncertain, largely because the specific versus subspecific status of some populations is unclear (Peralta and Spooner, 2000; Darwin et al., 2003; Peralta el al., 2005). As a result, several new species have been described in recent years (Darwin et al., 2003; Peralta et al., 2005). For example, taxonomists have recently (Darwin et al., 2003) described two very similar species, splitting the Galapagos tomato into the Hairy Galapagos tomato (*Solanum cheesmaniae*) and the Galapagos tomato (*Solanum galapagense*). The wild tomato clade thus includes some 10-15 species as described in current taxonomic literature. These are very closely-related, sharing a common ancestor from which they diverged no more than 7 million years ago (Nesbitt and Tanksley, 2002).

Some wild tomato species are known from small, localized populations that are isolated in restricted microhabitats distinguished by such factors as rainfall totals, soil types, and elevation (Rick, 1973; Peralta and Spooner, 2001). Warnock noted (1988) that the Andes encompass a diverse set of habitats which led to the observed adaptive differentiation of wild tomato species phenotypes.

The Galapagos have been known as a hotbed of biodiversity ever since Charles Darwin visited in 1835. It is well recognized that Darwin's five weeks in the Galapagos was one of the most significant events contributing to his formation of the theory of natural selection as the mechanism of biological evolution (*On the Origin of Species,* 1859). What is perhaps less well known is that Darwin collected thousands of species new to science during the five year voyage of the HMS Beagle. One of the species collected by Darwin was the endemic Galapagos tomato.

This plant still grows wild in the Galapagos, although pressures from human development as well as invasion by the weedy tomato variant (*S. esculentum* 'Gal cer') threaten many Galapagos tomato populations. The Galapagos tomato has been of interest to tomato breeders, as it extremely tolerant to high salt levels, as well as drought tolerant. In fact, the plants can still be found growing at the sea's edge, splashed by ocean spray, rooted in tiny patches of soil surrounded by dry lava, thriving in spite of overwhelmingly salty and arid conditions (personal observation. W. M.).

Several researchers (Peralta and Spooner, 2001; Nesbitt and Tanksley, 2002; Nuez el al., 2004; Peralta et al., 2006) have demonstrated that the Galapagos tomato is closely related to the wild species of the Andes. In fact, phylogenetic analysis shows that the Galapagos tomato is deeply nested within the clade of wild Andean tomatoes, one of which was the progenitor of the cultivated tomato. This clade includes *Solanum pimpinellifolium, S. hirsutum, S. pennellii, S. chmieleswskii, S. peruvianum*, and *S. chilense.*

This phylogenetic nesting of the Galapagos tomato is important, as in this tightly nested clade, only the Galapagos tomato exhibits robust salinity tolerance (Moyle, 2008), which suggests that this trait developed as a result of selective pressures specific to the Galapagos environment. Thus, it is clear that its ancestor must have arrived in the Galapagos and managed to adapt to saline, dry conditions. Every native plant species in Galapagos today is the descendent of an ancestral population that upon arrival, adapted successfully. Thus we see in extant species the track record of only successful colonization events, just as is true for crop plant domestications; only the winners contributed their adapted, positively selected genes. Nuez el al. (2004) document that the introduction of the ancestral Galapagos tomato occurred at least 1 million years ago, perhaps as much as 2 million years ago.

Whether seeds of the ancestral plant arrived by rafting from the mainland, as did the ancestors of most of the many endemic Galapagos species, or by wind, or was perhaps transported by birds, either adhering to their feet or feathers, or in fecal droppings, it is clear that the ancestral population was small, and was immediately subjected to strong selective pressures to deal with drought and salt levels that mainland wild species do not face. Such a strong selective event leaves a distinctive signature on the genes that are responsible for conferring the new adaptive traits that permit survival, indicated by Ka/Ks ratios >1 as discussed elsewhere herein.

Similar strong selective pressure occurred during plant domestication by humans: a small progenitor population, subject to overwhelming human-imposed selection pressure, leaves its mark.

A gene (fw2.2) that affects tomato fruit weight was reported by Frary et al. (2000). The fw2.2 QTL accounts for increases in fruit weight (Nesbitt and Tanksley, 2002) between heavy and lighter-weighted fruits, but as Nesbitt and Tanksley note, it is but one of a number of fruit size genes believed to exist in tomato. The fw2.2 cell-cycle gene does not explain fruit size as a result of protein-coding differences (Grandillo et al. 1999), which could be interpreted as a caution that our search for protein coding genes for this trait is risky. However, our previous work indicates that both expression/regulatory and protein coding differences are important to adaptation. Recently, another gene that affects fruit size in tomato, the YABBY-like transcription factor, was also identified by Tanksley's team (Cong et al., 2008). Regulatory changes of this transcription factor influence carpel number in tomato flower and fruit (Cong et al., 2008). In addition to fruit size, a gene that affects tomato morphology has also recently been identified (Xiao et al., 2008). Increased expression of SUN gives rise to an elongated fruit shape.

Like yield, the genes controlling drought and salinity tolerance pathways are not clear. It is recognized that the physiological mechanisms of salt tolerance are unusually complex and multigenic (Flowers, 2004). How salt uptake by plants occurs remains unclear, and molecular mechanisms of salt tolerance are especially uncertain (Sairam and Tyagi, 2004; Munns and Tester, 2008). Discovery of adapted salt tolerance genes, besides having immediate commercial value for the development of salt tolerant cultivated plants, may guide our greater understanding of the biology of how plants deal with salt. In addition, salt and drought tolerance are thought to share mechanisms, so salt-tolerance genes may also be used to confer drought tolerance on cultivated plants.

Tackling salinity tolerance in plants by cloning known genes that are up or down regulated in response to salt can be very frustrating because of the homeostasis that thwarts any changes in flow through conserved pathways. Oftentimes positively selected genes are not the key pathway enzymes, but distant control points that would not have been a priori obvious to scientific investigators. Finding the vulnerable place to open the taps in a pathway is thus not often determinable by logical processes. Nature is the ultimate "systems biology" platform, adapting organisms while taking into account their full complexity. Successful adaptation of a gene indicates that protein coding changes at that particular gene were not deleterious, and suggests that that particular gene should be amenable to further "adaptation" or change to further enhance an adapted trait.

Attempts in the 1930s (Flowers, 2004) to breed salinity tolerance into the cultivated tomato by crossing with the salt tolerant Galapagos tomato were unsuccessful. This suggests that having in hand the actual adapted salt tolerance genes, with a track record of change, is the critical factor. As mentioned above, salt tolerance is a multigenic trait. Not all genes that impact a trait are positively selected, just key control genes. The genes could be used as either for MAB (marker-assisted breeding), to gain more precision in guiding the movement of the salt tolerance trait into cultivated tomato, or alternatively in a transgenic approach in which the Galapagos tomato salinity or drought tolerance gene(s) is transformed into cultivated tomato. It is known that salt tolerance, like yield, is a multigene trait (Flowers, 2004). We found a very few critical genes in our search for yield control genes: this handful of genes apparently influences a number of others; this may be true for salt tolerance as well.

*Vitis* (Grape Vines)

Grapevines (*Vitis vinifera*) are a fruit bearing woody vines. The grapevine plant is popular for its fruits which grow in clusters of 15 to 300 grapes and can be found in a wide array of colors ranging from crimson black, dark blue, yellow, green, orange, and pink. The fruit of the plant can be eaten raw, but is also commonly used for making wine, jam, juice, jelly, grape seed extracts, raisins, vinegar, and grape seed oil. The grapevine plant is known as one of the earliest domesticated plant species, dating back over 6,000 years. Together with yeast, grapes are mainly known for their use in wine making. Ancient Egyptian hieroglyphics record the cultivation of purple grapes the history of the ancient Greeks and Phoenicians is riddled with references to grape cultivation.

According to the Food and Agriculture Organization (FAO), grapevines account for about 18,746,900 acres of arable land, with approximately 71% of the world's grape production being used for the production of wine. The world grape production for 2012 was estimated at 67,067,128 metric tons. Top producers of grapes include China, the U.S. Italy, France, and Spain.

One important development for table grape consumption has been the production of seedless grapes. These fruits produce small, immature seeds which do not have the hard seed coat which is undesirable for consumers. There are many genetic sources for seedless grapes including 'Thomson Seedless', 'Russian Seedless', and 'Black Monukka' varieties among others. A non-exhaustive list of known "White" grapes include: 'Addoraca', 'Arbane', 'Pinot Jaune', 'Moscatel', 'Chardonnay', 'Carignan blanc', 'Zinfandler', 'Sauvignon blanc', 'Moscato', 'Juwel', 'Kanzler', 'Siegerrebe', 'Buonamico', among others. A non-exhaustive list of table grapes includes: 'Black Corinth'. 'Black Monukka'. 'Cardinal', 'Red Corinth'. 'Valencia'. 'Red Flame', 'Diamond', 'Perlette'. 'Sugarone', 'Sultana', 'White Corinth'. Other popular grape varieties include: 'Catawba', 'Concord', 'Einset', 'Emperor', 'Canadice', 'Ruby Roman', 'Ruby Seedless', 'Ederena' among many others (see Reisch et al., 1993 "Wine and Juice Grape Varieties for Cool Climates" Cornell Cooperative Information Bulletin 233).

Grape's 1C genome size is approximately 480 mega base pairs. Grape has 19 chromosomes (2n=38). Although most grapes are diploid (2n), tetraploid and triploid plants have also been identified. The grape genome has been sequenced and multiple browsers are available online (see Jaillon et al., "The grapevine genome sequence suggests ancestral hexaploidization in major angiosperm phyla" Nature, 449: 463-467). Additionally, several methods of transformation have been developed Li et al (2008) "An improved protocol for *Agrobacterium*-mediated transformation of grapevine (*Vitis vinifera* L.)" Plant Cell Tiss Organ Cult; Perl et al (1996) "Establishment of an *Agrobacterium*-mediated transformation system for grape (*Vitis vinifera* L.): The role of antioxidants during grape-*Agrobacterium* interactions" Nat Bio 14 624-628.

Most cultivated grapes produce perfect flowers with both pistil and anther production in the same flower. Grape crosses can be conducted either by hand pollination or by intertwining grape vines (usually grown in movable pots) to create cross fertilization. A more thorough description of grape breeding can be found in Alleweldt et al., (1988) "Progress in grapevine breeding" Theoretical and Applied Genetics Vol 75, 5 669-673.

EGTom1 and/or EGTom2 Proteins

The present invention also provides polypeptides and amino acid sequences comprising at least a portion of the isolated proteins encoded by nucleotide sequences for EGTom1 and/or EGTom2, homologs of EGTom1 and/or EGTom2, orthologs of EGTom1 and/or EGTom2, paralogs of EGTom1 and/or EGTom2, and fragments and variations thereof.

The present invention also provides an isolated amino acid sequence encoded by the nucleic acid sequences of EGTom1 (SEQ ID NO: 1) and/or EGTom2 (SEQ ID NO: 2), homologs of EGTom1 and/or EGTom2, orthologs of EGTom1 (SEQ ID Nos: 3 and 4) and/or EGTom2 (SEQ ID Nos: 5 and 6), paralogs of EGTom1 and/or EGTom2, and/or fragments and variations thereof. In some embodiments, the present invention provides an isolated polypeptide comprising an amino acid sequence that shares at least about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of EGTom1 and/or EGTom2, homologs of EGTom1 and/or EGTom2, orthologs of EGTom1 and/or EGTom2, paralogs of EGTom1 and/or EGTom2, and/or fragments and variations thereof. In one embodiment, the present invention provides an isolated polypeptide comprising an amino acid sequence which encodes an amino acid sequence that shares at least about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of EGTom1 and/or EGTom2, homologs of EGTom1 and/or EGTom2, orthologs of EGTom1 and/or EGTom2, paralogs of EGTom1 and/or EGTom2, and/or fragments and variations thereof.

The invention also encompasses variants and fragments of proteins of an amino acid sequence encoded by the nucleic acid sequences of EGTom1 and/or EGTom2, homologs of EGTom1 and/or EGTom2, orthologs of EGTom1 and/or EGTom2 and/or paralogs of EGTom1 and/or EGTom2. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both.

Functional fragments and variants of a polypeptide include those fragments and variants that maintain one or more functions of the parent polypeptide. It is recognized that the gene or cDNA encoding a polypeptide can be considerably mutated without materially altering one or more of the polypeptide's functions. First, the genetic code is well-known to be degenerate, and thus different codons encode the same amino acids. Second, even where an amino acid substitution is introduced, the mutation can be conservative and have no material impact on the essential function(s) of a protein. See, e.g., *Stryer Biochemistry* 3' Ed., 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *J. Immunol.* 159(5): 2502-12, 1997). Other modifications that can be made without materially impairing one or more functions of a polypeptide can include, for example, in vivo or in vitro chemical and biochemical modifications or the incorporation of unusual amino acids. Such modifications include, but are not limited to, for example, acetylation, carboxylation, phosphorylation, glycosylation, ubiquination, labelling, e.g., with radionucleotides, and various enzymatic modifications, as will be readily appreciated by those well skilled in the art. A variety of methods for labelling polypeptides, and labels useful for such purposes, are well known in the art, and include radioactive isotopes such as $^{32}P$, ligands which bind to or are bound by labelled specific binding partners (e.g., antibodies), fluorophores, chemiluminescent agents, enzymes, and anti-ligands. Functional fragments and variants can be of varying length. For example, some fragments have at least 10, 25, 50, 75, 100, 200, or even more amino acid residues. These mutations can be natural or purposely changed. In some embodiments, mutations containing alterations that produce silent substitutions, additions, or deletions, but do not alter the properties or activities of the proteins or how the proteins are made are an embodiment of the invention.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (*J. Bacteriol.*, 169:751-757, 1987), O'Regan et al. (*Gene,* 77:237-251, 1989), Sahin-Toth et al. (*Protein Sci.,* 3:240-247, 1994), and Hochuli et al. (*Bio/Technology,* 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., *Proc. Natl. Acad. Sci. USA,* 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following Table 1 shows exemplary conservative amino acid substitutions.

TABLE 1

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |

TABLE 1-continued

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some examples, variants can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, Ile, Val, Met, Phe, or Trp) in a variant sequence can be replaced with a different hydrophobic residue (such as Leu, Ile, Val, Met, Phe, or Trp) to create a variant functionally similar to the disclosed an amino acid sequences encoded by the nucleic acid sequences of EGTom1 and/or EGTom2, homologs of EGTom1 and/or EGTom2, orthologs of EGTom1 and/or EGTom2 and/or paralogs of EGTom1 and/or EGTom2, and/or fragments and variations thereof.

In some embodiments, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed an amino acid sequences encoded by the nucleic acid sequences of EGTom1 and/or EGTom2, homologs of EGTom1 and/or EGTom2, orthologs of EGTom1 and/or EGTom2 and/or paralogs of EGTom1 and/or EGTom2, and/or fragments and variations thereof.

In some embodiments, functional fragments derived from the EGTom1 and/or EGTom2 orthologs of the present invention are provided. Examples of EGTom1 orthologs are provided by SEQ ID NO: 3 and SEQ ID NO: 4. Examples of EGTom2 orthologs are provided by SEQ ID NO: 5 and SEQ ID NO: 6. The functional fragments can still confer salt tolerance, drought tolerance and/or increase or decrease sugar content of fruit (sweetness) when expressed in a plant. In some embodiments, the functional fragments contain at least key domains of a wild type EGTom1 and/or EGTom2 orthologs, or functional variants thereof. In some embodiments, the functional fragments contain one or more conserved region shared by two or more EGTom1 and/or EGTom2 orthologs, shared by two or more EGTom1 and/or EGTom2 orthologs in the same plant genus, shared by two or more dicot EGTom1 and/or EGTom2 orthologs, and/or shared by two or more monocot EGTom1 and/or EGTom2 orthologs. The key domain or conserved regions can be determined by any suitable computer program, such as NCBI protein BLAST program and NCBI Alignment program, or equivalent programs. In some embodiments, the functional fragments are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids shorter compared to the EGTom1 and/or EGTom2 orthologs of the present invention. In some embodiments, the functional fragments are made by deleting one or more amino acid of the EGTom1 and/or EGTom2 orthologs of the present invention. In some embodiments, the functional fragments share at least 80%, 85%, 90%, 95%, 96%, 97%, 98%, 99%, or more identity to the EGTom1 and/or EGTom2 orthologs of the present invention.

SEQ ID No's 7-12, and 14, are the polypeptide sequences encoded in the nucleic acid sequences of SEQ ID No's 1-6, and 13.

In some embodiments, functional chimeric or synthetic polypeptides derived from the EGTom1 and/or EGTom2 orthologs of the present invention are provided. The functional chimeric or synthetic polypeptides can still confer salt tolerance, drought tolerance and/or increased or decreased sugar content of fruit (sweetness) when expressed in a plant. In some embodiments, the functional chimeric or synthetic polypeptides contain at least the key domains of a wild type EGTom1 and/or EGTom2 orthologs, or functional variants thereof. In some embodiments, the functional chimeric or synthetic polypeptides contain one or more conserved region shared by two or more EGTom1 and/or EGTom2 orthologs, shared by two or more EGTom1 and/or EGTom2 orthologs in the same plant genus, shared by two or more dicot EGTom1 and/or EGTom2 orthologs, and/or shared by two or more monocot EGTom1 and/or EGTom2 orthologs. The domain or conserved regions can be determined by any suitable computer program, such as NCBI protein BLAST program and NCBI Alignment program, or equivalent programs. In some embodiments, the functional chimeric or synthetic polypeptides share at least 80%, 85%, 90%, 95%, 96%, 97%, 98%, 99%, or more identity to the EGTom1 and/or EGTom2 orthologs of the present invention.

Sequences of conserved regions can also be used to knock-down the level of one or more EGTom1 and/or EGTom2 orthologs. In some embodiments, sequences of conserved regions can be used to make gene silencing molecules to target one ore more EGTom1 and/or EGTom2 orthologs. In some embodiments, the gene silencing molecules are selected from the group consisting of double-stranded polynucleotides, single-stranded polynucleotides or Mixed Duplex Oligonucleotides. In some embodiments, the gene silencing molecules comprises a DNA/RNA fragment of about 10 bp, 15 bp, 19 bp, 20 bp, 21 bp, 25 bp, 30 bp, 40 bp, 50 bp, 60 bp, 70 bp, 80 bp, 90 bp, 100 bp, 150 bp, 200 pb, 250 bp, 300 bp, 350 bp, 400 bp, 500 bp, 600 bp, 700 bp, 800 bp, 900 bp, 1000 bp, or more polynucleotides, wherein the DNA/RNA fragment share at least 90%, 95%, 99%, or more identity to a conserved region of the EGTom1 and/or EGTom2 orthologs sequences of the present invention, or complementary sequences thereof.

Plant Transformation

The present polynucleotides coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof the present invention can be transformed into tomato or other plant genera.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538.877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996): Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E.I. du Pont de Nemours and Company. Most species of plants have been transformed using this method.

The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556. EP0270822, WO8504899, WO8603516. U.S. Pat. No. 5,591,616, EP0604662, EP0672752, WO8603776. WO9209696, WO9419930, WO9967357, U.S. Pat. No. 4,399,216, WO8303259, U.S. Pat. No. 5,731,179, EP068730, WO9516031, U.S. Pat. No. 5,693,512, U.S. Pat. No. 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. No. 5,204,253, U.S. Pat. No. 5,015,580). A third direct method uses fibrous forms of metal or ceramic consisting of sharp, porous or hollow needle-like projections that literally impale the cells, and also the nuclear envelope of cells. Both silicon carbide and aluminium borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767, 378; U.S. Pat. No. 5,994,629). More typically, however, negative selection is used because it is more efficient, utilizing selective agents such as herbicides or antibiotics that either kill or inhibit the growth of non-transformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. No. 5,034,322, U.S. Pat. No. 6,174,724 and U.S. Pat. No. 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet 79:

625-631(1990), U.S. Pat. No. 4,795,855, U.S. Pat. No. 5,378,824 and U.S. Pat. No. 6,107,549). In addition, the dhfr gene, which confers resistance to the anticancer agent methotrexate, has been used for selection (Bourouis et al., EMBO J. 2(7): 1099-1104 (1983).

Non-limiting examples of binary vectors suitable for tomato species transformation and transformation methods are described by Antonio Di Matteo et al. (2011) Genetic Transformation in Tomato: Novel Tools to Improve Fruit Quality and Pharmaceutical Production, Genetic Transformation, Prof. Maria Alvarez (Ed.). ISBN: 978-953-307-364-4, InTech, or by similar experimental procedures well known to those skilled in the art. Tomato plants can be transformed by using any method described in the above references.

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed. DNA sequences which direct polyadenylation of the RNA are also commonly added to the vector construct. Polyadenylation sequences include, but are not limited to the *Agrobacterium* octopine synthase signal (Gielen et al., EMBO J 3:835-846 (1984)) or the nopaline synthase signal (Depicker el al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as improved fatty acid composition, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods to Evaluate Evolutionary Significance of Nucleotide Changes

Any of several different molecular evolution analyses or Ka/Ks-type methods can be employed to evaluate quantitatively and qualitatively the evolutionary significance of the identified nucleotide changes between homologous gene sequences from related species. Kreitman and Akashi (1995) Annu. Rev. Ecol. Syst. 26:403 422; Li, Molecular Evolution, Sinauer Associates, Sunderland, Mass., 1997. For example, positive selection on proteins (i.e., molecular-level adaptive evolution) can be detected in protein-coding genes by pairwise comparisons of the ratios of non-synonymous nucleotide substitutions per non-synonymous site (Ka) to synonymous substitutions per synonymous site (Ks) (Li et al., 1985; Li, 1993). Any comparison of Ka and Ks may be used, although it is particularly convenient and most effective to compare these two variables as a ratio. Sequences are identified by exhibiting a statistically significant difference between Ka and Ks using standard statistical methods.

Preferably, the Ka/Ks analysis by Li et al. is used to carry out the present invention, although other analysis programs that can detect positively selected genes between species can also be used. Li et al. (1985) Mol. Biol. Evol. 2:150 174; Li (1993); see also J. Mol. Evol. 36:96 99; Messier and Stewart (1997) Nature 385:151 154; Nei (1987) Molecular Evolutionary Genetics (New York, Columbia University Press). The Ka/Ks method, which comprises a comparison of the rate of non-synonymous substitutions per non-synonymous site with the rate of synonymous substitutions per synonymous site between homologous protein-coding regions of genes in terms of a ratio, is used to identify sequence substitutions that may be driven by adaptive selections as opposed to neutral selections during evolution. A synonymous ("silent") substitution is one that, owing to the degeneracy of the genetic code, makes no change to the amino acid sequence encoded; a non-synonymous substitution results in an amino acid replacement. The extent of each type of change can be estimated as Ka and Ks, respectively, the numbers of synonymous substitutions per synonymous site and non-synonymous substitutions per non-synonymous site. Calculations of Ka/Ks may be performed manually or by using software. An example of a suitable program is MEGA (Molecular Genetics Institute, Pennsylvania State University).

For the purpose of estimating Ka and Ks, either complete or partial protein-coding sequences are used to calculate total numbers of synonymous and non-synonymous substitutions, as well as non-synonymous and synonymous sites. The length of the polynucleotide sequence analyzed can be any appropriate length. Preferably, the entire coding sequence is compared, in order to determine any and all significant changes. Publicly available computer programs, such as Li93 (Li (1993) J. Mol. Evol. 36:96 99) or INA, can be used to calculate the Ka and Ks values for all pairwise comparisons. This analysis can be further adapted to examine sequences in a "sliding window" fashion such that small numbers of important changes are not masked by the whole sequence. "Sliding window" refers to examination of consecutive, overlapping subsections of the gene (the subsections can be of any length).

The comparison of non-synonymous and synonymous substitution rates is commonly represented by the Ka/Ks ratio. Ka/Ks have been shown to be a reflection of the degree to which adaptive evolution has been at work in the sequence under study. Full length or partial segments of a coding sequence can be used for the Ka/Ks analysis. The higher the Ka/Ks ratio, the more likely that a sequence has undergone adaptive evolution and the non-synonymous substitutions are evolutionarily significant. See, for example, Messier and Stewart (1997).

Ka/Ks ratios significantly greater than unity strongly suggest that positive selection has fixed greater numbers of amino acid replacements than can be expected as a result of chance alone, and is in contrast to the commonly observed pattern in which the ratio is less than or equal to one. Nei (1987); Hughes and Nei (1988) *Nature* 335:167 170; Messier and Stewart (1994) *Current Biol.* 4:911 913; Kreitman and Akashi (1995) *Ann. Rev. Ecol. Syst.* 26:403 422; Messier and Stewart (1997). Ratios less than one generally signify the role of negative, or purifying selection: there is strong pressure on the primary structure of functional, effective proteins to remain unchanged.

All methods for calculating Ka/Ks ratios are based on a pairwise comparison of the number of non-synonymous substitutions per non-synonymous site to the number of synonymous substitutions per synonymous site for the protein-coding regions of homologous genes from related species. Each method implements different corrections for estimating "multiple hits" (i.e., more than one nucleotide substitution at the same site). Each method also uses different models for how DNA sequences change over evolutionary time. Thus, preferably, a combination of results from different algorithms is used to increase the level of sensitivity for detection of positively-selected genes and confidence in the result.

It is understood that the methods described herein could lead to the identification of tomato polynucleotide sequences that are functionally related to tomato protein-coding sequences. Such sequences may include, but are not limited to, non-coding sequences or coding sequences that do not encode proteins. These related sequences can be, for example, physically adjacent to the tomato protein-coding sequences in the tomato genome, such as introns or 5'- and 3'-flanking sequences (including control elements such as promoters and enhancers). These related sequences may be obtained via searching a public genome database such as GenBank or, alternatively, by screening and sequencing an appropriate genomic library with a protein-coding sequence as probe. Methods and techniques for obtaining non-coding sequences using related coding sequence are well known to one skilled in the art.

After candidate genes were identified, the nucleotide sequences of the genes in each orthologous gene pair are carefully verified by standard DNA sequencing techniques and then completed Ka/Ks analysis for each carefully sequenced candidate gene pair.

Breeding Methods

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids.

A hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176. In Hybridization of Crop Plants.

Bulk Segregation Analysis (BSA).

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*. 99:9828-9832) and Quarrie et al. (Quarrie et al., Bulk segregant analysis with molecular markers and its use for improving drought resistance in maize, 1999*, Journal of Experimental Botany,* 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding.

The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

RNA Interference (RNAi)

RNA interference (RNAi) is the process of sequence-specific, post-transcriptional gene silencing or transcriptional gene silencing in animals and plants, initiated by double-stranded RNA (dsRNA) that is homologous in sequence to the silenced gene. The preferred RNA effector molecules useful in this invention must be sufficiently distinct in sequence from any host polynucleotide sequences for which function is intended to be undisturbed after any of the methods of this invention are performed. Computer algorithms may be used to define the essential lack of homology between the RNA molecule polynucleotide sequence and host, essential, normal sequences.

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of nucleic acid sequences coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof, or an opposite strand replication intermediate. In one embodiment, said double-stranded RNA effector molecules are provided by providing to a tomato or other plant, plant tissue, or plant cell an expression construct comprising one or more double-stranded RNA effector molecules. In one embodiment, the expression construct comprises a double-strand RNA derived from any one of nucleic acid sequences coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof. In other embodiments, the expression construct comprises a double-strand RNA derived from more than one sequences of nucleic acid sequences coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof. In further embodiments, the expression construct comprises a double-strand RNA derived from more than one sequences of nucleic acid sequences coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof, and one or more other genes involved in salt tolerance, drought tolerance and/or sugar content of fruit (sweetness). One skilled in the art will be able to design suitable double-strand RNA effector molecule based on the nucleotide sequences of nucleic acid sequences coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof in the present invention.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 500 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 250-500 bp, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

The expression construct of the present invention comprising DNA sequence which can be transcribed into one or more double-stranded RNA effector molecules can be transformed into a plant, wherein the transformed plant produces different fatty acid compositions than the untransformed plant. The target sequence to be inhibited by the dsRNA effector molecule include, but are not limited to, coding region, 5' UTR region, 3' UTR region of fatty acids synthesis genes. In one embodiment, the target sequence is from one or more nucleic acid sequences coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof.

The effects of RNAi can be both systemic and heritable in plants. In plants, RNAi is thought to propagate by the transfer of siRNAs between cells through plasmodesmata. The heritability comes from methylation of promoters targeted by RNAi; the new methylation pattern is copied in each new generation of the cell. A broad general distinction between plants and animals lies in the targeting of endogenously produced miRNAs; in plants, miRNAs are usually perfectly or nearly perfectly complementary to their target genes and induce direct mRNA cleavage by RISC, while animals' miRNAs tend to be more divergent in sequence and induce translational repression. Detailed methods for RNAi in plants are described in David Allis et al (Epigenetics, CSHL Press, 2007, ISBN 0879697245, 9780879697242). Sohail et al (Gene silencing by RNA interference: technology and application, CRC Press, 2005, ISBN 0849321417, 9780849321412), Engelke et al. (RAN Interference, Academic Press, 2005, ISBN 0121827976, 9780121827977), and Doran et al. (RNA Interference: Methods for Plants and Animals, CABI, 2009, ISBN 1845934105, 9781845934101), which are all herein incorporated by reference in their entireties for all purposes.

The present invention provides methods of producing tomatoes or other plants containing altered salt tolerance, drought tolerance and/or sugar content of fruit (sweetness). Such methods comprise utilizing the tomato or other plants comprising the chimeric genes as described above.

The present invention also provides methods of breeding tomato and other plants producing altered salt tolerance, drought tolerance and/or sugar content of fruit (sweetness). In one embodiment, such methods comprise:

i) making a cross between the tomato or other plant species with nucleic acid sequences coding for EGTom1 and/or EGTom2, homologs of EGTom1 and/or EGTom2, orthologs of EGTom1 and/or EGTom2 and/or paralogs of EGTom1 and/or EGTom2, and/or fragments and variations thereof as described above to a second tomato or other plant species to make F1 plants;

ii) backcrossing said F1 plants to said second tomato or plant species, respectively;

iii) repeating backcrossing step until said nucleic acid sequences are integrated into the genome of said second tomato or other plant species, respectively. Optionally, such method can be facilitated by molecular markers.

The present invention provides methods of breeding species close to *Solanum esculentum*, wherein said species produces altered salt tolerance, drought tolerance and/or sugar content of fruit (sweetness). In one embodiment, such methods comprise i) making a cross between the non-*Solanum esculentum* species containing nucleic acid sequences coding for homologs of EGTom1 and/or EGTom2, orthologs of EGTom1 and/or EGTom2 and/or paralogs of EGTom1 and/or EGTom2, and/or fragments and variations thereof as described above to *Solanum esculentum* to make F1 plants;

ii) backcrossing said F1 plants to *Solanum esculentum;* iii) repeating backcrossing step until said nucleic acid sequences are integrated into the genome of *Solanum esculentum*. Special techniques (e.g., somatic hybridization) may be necessary in order to successfully transfer a gene from non-*Solanum esculentum* species to *Solanum esculentum*. Optionally, such method can be facilitated by molecular markers.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1. Identification of Salt/Drought Tolerance and Fruit Sugar Content Genes in Tomato EST sequences representing the expressed genes of the cultivated tomato genome were obtained from GenBank.

As discussed in more detail herein, the Galapagos tomato (*Solanum cheesmaniae*) transcriptome was sequenced, Ka/Ks analysis of homologous gene pairs between cultivated tomato and Galapagos tomato were performed, and preliminary validation was done to show that the positively selected tomato genes that were identified likely have roles in salt/drought tolerance or in controlling fruit sugar content.

All tissues were collected from Galapagos tomato plants (*S. cheesmaniae*) grown from seeds from the C.M. Rick Tomato Genetics Resource Center (TGRC). Seed germination success was enhanced by soaking seeds in a dilute (1%) bleach solution for 24 hours.

RNAs were pooled from multiple tissues (including roots, stems, flowers and fruit) and multiple life stages of the Galapagos tomato plants grown at our facility. While this strategy means that some redundancy in ESTs can be expected, normalization during library construction makes this manageable. These tissues included multiple root tissues, as the root represents the interface at which the plant most directly first confronts salinity issues.

cDNA libraries were constructed from the RNA obtained from *S. cheesmaniae* and 180,000 reads were completed. This gives multiple-fold coverage to enhance the odds for sampling the vast majority of expressed genes. Ka/Ks analysis was conducted as sequence data become available. A proprietary automated pipeline was used that takes each new EST sequence, BLASTs against sequences in GenBank, and conducts pairwise comparisons of Ka/Ks. ESTs contain some level of sequencing errors, so potential candidate genes identified were then re-sequenced.

This experimental work yielded a preliminary set of 10 potential candidate genes for salt/drought tolerance from the Galapagos tomato (*Solanum cheesmaniae/galapagense*). These all appeared to be positively selected genes, as compared to their orthologs from the close relative, cultivated tomato (*S. esculentum*). However, re-sequencing and phylogenetic analysis narrowed the field to two candidates: both very strongly positively selected. The data suggested that one gene may control drought/salinity tolerance, and the second likely controls fruit sugar content.

EGTom1 and/or EGTom2 tomato sequences follow. Initiation codons are shown in underlined lower case font. Termination codons are shown in bolded lower case font. The UTR sequence is shown in lower case.

Galapagos tomato (*Solanum chessmanii*) coding sequence for EGTom1 (salt/drought tolerance) (SEQ ID NO: 1):

atgGAGAATAATAAAGGAAATGCTGAGAGTAATGAGGACAGTCATATCA

CACCCAGCACGAAGAAAACTCACGCGCTTCAACAAAATGGCGTGGAGAA

TATAGAGGCGCCCCCCAACTCTGATGCGACTAAAAAAAAGGGCCCCAGT

AGAAGTGCCAAGAGAAAATCTGCTAAAAGAAGATGGTTGCGAGAGATGG

CCAAAATTAAGGAGAAGAATGCAGATGCTGAATCGGAAGGGCTGCGGAA

CTGGAAAGAAATGCAGGCTAAAGCTGGAAAGGGAGAGCCTAGCTGCCAA

CCAAAGGGGCGATTGAATGACGGGGCTAATGGTCACCGAAATGGGAAGC

AGCAGAAAACTAAAACTAAAAAAGAGAGGTAACTGGCCAACCAAAGGGA

CTTCTGCATAGGAAGCAATTCCATAGTGAAGATAAGAATGGAGATACAA

ACGAAGAAAAGCAAGCAGAAGAGAAAAGCAAATCATGTGGACAATCATG

TCAAAATAGTGACTCAGAAGATGAAGTTGTTCCAGTTGAAATAAGGCCT

GGGCATATTCGCTTTGAACCTGTTGGAAAAGAACAAGTTTCAAAGCAGA

GTGAAGAAGAAATGGAAAGTTTCAAGTGGAATGGTATGATGAGCAAGAA

AAAGGGACAGAAATGGGGCCAAGAGAAAGTTTCATTTCCCCAAAAGACT

GATTCTCTAGGTTCAAACAAAGAATATCCTGATATGATGAGTCGTGAGA

GACAGAAATGGATCCAAGAGAAAGACTCATTTTCCCAAAAGAATGATTC

CCTTAGTTCAAACAAAGAACATCCTGAGATAATGAATCGTAAAAGACAG

-continued

AAATGGGGCCAAGAGAATATTTCATTTGCCCAAAAGAATGATTCTCCAG

GTTCAAGCAAAGAACATCCTGATATGATGAACCGTGAGAGACAGAAATG

GAGCCAAGAGAAAAACTTGTTTTACCAAAAGAATGATTCTCTCGGTTCA

AACAAAGAACATCCCGAGATAATGAATCGTAATAGACAGAACTGGGGCG

AAGAGAATGTTTCATTTTCCCAAAAGAATGATTCTCTAGATTCAAACAA

AAAACATCCTGAGATGTTGAATGGTGAAAAGGAGCCTCATTTCAATGGA

TCAATTGACTTCAATACACTTCCTTTTCTTTCTGGCCAGCCCAAGGAAG

GTCTTGTGATTGCATATCGGCTGETTGAGTTATCATCAACCTGGACCCC

TGAAGTTTCCTCCTATCGGGTTGGGAAAATATCATCGTATAATTCTGAA

GCAAATAGAGTTTTGCTGATGCCAGTAGCTGAATTTCCAGTCATTTGTA

CTGAGGATGAGTCTTCAAAGCAACCAGATAGCTCTATTTATAATGAAGA

CGGATCTTTGGAGATAGAATTTTCAGCGCTTCTTGAAGTTCGTCTGATG

AATAGTACTCCAGATCAAGGAGTACATGAAGGGGTTATTGAGGGTTCTG

CTGCCAATGAGTCCACTCCAGTGCTTGGAAGCAGTAAAAAGAAAAATGA

AACTCCAGTTCCTGGAGCTGGAGAAGTAAGCAATGGAAAACAAACACGA

TCTACCCCTTCAGAAAATGGCGGAGTAAACCTGTGGGAGCAATTCAGTG

ATACTCTAAAGTCCAAGAAGGCAGAATTAGCTCAGGAAAGTAATTGGGA

TAAGGCAAGTACTGGAAAGAGCCCTTGGTCATATCGACCCATGAGAGGC

ACTGCGCTAGGCCCTACAATGGCCTTCCTTAGATCCCAAAAGAAAATA taa

Galapagos tomato (*Solanum chessmanii*) coding sequence for EGTom2 (sugar content in fruit) (SEQ ID NO: 2):

atgGAGAATTCGCGTGAGTTTCTAAGCAATGGAAAACCAGCTGATCCTGG

TCTTCAAATTATAAGGCACCCCTCTTACCAATCTTGTGGGAAATTATCG

TTATCTTGGTTTGATATTAGAGTATTTTACATCAGAATCAGCAATTTTA

TGGTCGATGATTCAACCCCAGAAATTCTTACGCTTAACCATATCCCTTT

AAGCCCCGATACACTGCTTGAAGTTAATGGTATAAGATGTTCAGTGCAC

TCGGAAGGAGCCTCTTGCTTTCTTCGAAGGGACCGTGTTGATAAGAAAG

CTGAAGAAGCTACATTTGTGAGCACAGATAGTATAAGATTGACTGGGAG

TGTGAACTTTGAGGTTTCATATAAAGATGATCTTTTTCTCTCTGGGACT

TTGGAGATGGCCAACATCAATGATTCTCAAAACTGTCTTAGGAGATGGA

GCATGAACTGTGAATCAGTTATGAGTGCTGGCACGGGATTTCTGAAAGG

AAAACATATTGTGGGTTCTGAATCATTGTCACCGACAATTGAAGTCTAT

GTTACCGGTTGCTTCTCTGGGACACCTATCATCTTAACTAAGACTTTGC

AGCTAAATCACAGGAAGAAGCACCATAGAAAGGGTATGTTAGACTCCAT

TCCGGAGCATGACACTTCTGAACAGCATAAAGAAGTCTCATCTGAACAT

GATCTGCAGGTAACAGAATACAACGGAAACTACAAACCAGAAAGCGAAG

AAGACTACAACAACATGTACTGGGGACGAACAGAACTTATGGATGGTGA

AGACGGAGAAATGTCCTGGTTCAATGCTGGGGTTCGAGTTGGTGTTGGG

ATTGGCCTTGGCATTTGTGTAGGAGTTGGAGTAGGAGTTGGTTTATTAG

TCCGTACTACACGCAACTTAAGAAGGCGCCTTATGtaa

We identified tomato genes that have undergone adaptive evolution between *S. esculentum* and *S. cheesmaniae*. As described herein, two adapted genes were identified, initial validation was performed, and the characterized allele structure of these genes was correlated in other well-characterized *Solanum* species. Based on these results, one of these candidate genes (i.e., EGTom1) impacts salt/drought tolerance, and that the second candidate gene controls fruit sugar content.

Example 2. Validation of Gene Function

The two candidate genes EGTom1 and EGTom2 were first investigated in silico; we BLASTed the sequences against the GenBank database in order to verify possible function (both biochemical and in the organism).

EGTom1 codes for a protein that is homologous to proteins known to participate in drought stress-response pathways.

BLAST results for EGTom2 recovered ESTs from several different species, including both dicots and monocots. Many ESTs were recovered for tomato; nearly all were from tomato fruits, and a few from tomato flowers in later stages of development. Another frequent source for EST orthologs of EGTom2 was the wine grape (*Vitis vinifera*). The EGTom ortholog discovered in wine grape is included in (SEQ ID NO: 13).

The most common sources of monocot EST hits for EGTom2 were sugarcane (*Saccharum officinarum*) and corn kernels (*Zea mays*). EGTom2 showed homology to genes that code for a subset of hydroxyacid dehydrogenase proteins. The scientific literature suggests that these proteins are involved in sugar metabolism. Thus, this is all is a good indication that EGTom2 may be a fruit sugar control gene.

Example 3. Transformation of Tomato with EGTom1 and/or EGTom2

The two candidate genes EGTom1 and EGTom2 were cloned into appropriate expression vectors for use in transgenic tomatoes.

Transgenic cultivated tomato (var. 'Micro-Tom') will be prepared using the different alleles found for each positively selected gene (i.e., EGTom1 and EGTom2) and the impact of specific alleles will be measured on drought/salt-tolerance, and fruit sugar content, respectively.

Cultivated tomato plants can be transformed with a construct containing EGTom1 and/or EGTom2 using standard transformation technology for tomato plants. Sec, e.g., Antonio Di Matteo et al. (2011) Genetic Transformation in Tomato: Novel Tools to Improve Fruit Quality and Pharmaceutical Production, Genetic Transformation, Prof. Maria Alvarez (Ed.), ISBN: 978-953-307-364-4, InTech.

The EGTom1-transformed 'Micro-Tom' plants can be tested for salt/drought tolerance and the EGTom2-transformed 'Micro-Tom' plants can be tested for fruit sugar content compared to the untransformed, control 'Micro-Tom' tomato plants.

Example 4. EGTom2 Transformation and Transgenic Analysis

As originally described in Example 3, an expression vector containing EGTom2 was transformed into 'Micro Tom' tomatoes (a tomato cultivar commonly used for transformation experiments). Primary transformants were produced for two groups: a set of control plants that contained only the transformed expression vector, and a second set of experimental plants that contained overexpression vectors with EGTom2. The EGTom2 gene was first identified in the Galapagos tomato (*Solanum cheesmaniae*).

Control plants were analyzed for any effects that could be ascribed solely to the transformation process, e.g., yield depression, unusual growth patterns, aberrant sweetness levels, etc. No aberrant effects were noted.

EGTom2 gene expression levels in the experimental group of primary transformants were estimated by quantitative real-time RT-PCR, giving copy number per ng of RNA. Transformants EGTom2-6, EGTom2-14, and EGTom2-19 all displayed very high copy number of the EGTom2 gene (all over 300 copy/ng). EGTom2-6, in particular, had over 500 copying. In contrast, low copy number (approx. 100-180 copy/ng), and thus low expression levels of EGTom2, were found in EGTom2-2, EGTom2-8. EGTom2-11, and EGTom2-26. EGTom2-21 displayed an intermediate level of expression, approximately 250 copy/ng.

Primary transformants were then grown to the fruit set stage. Brix levels (a measure of soluble sugars) were then measured for the fruits from the primary transformant plants. Results are shown in FIG. 1. Transformants with high copy number of EGTom2 exhibited Brix values of about 5 or greater, easily surpassing the untransformed control tomato variety 'Flora-Dade', a popular variety prized for its sweetness and hardiness. Perhaps the most exciting result is that EGTom2-6, which had by far the highest level of expression of the SC-1 gene (>500 copy/ng) also showed the highest Brix values, measured at 5.5 suggesting a dose dependent effect for EGTom2 expression and sweetness. Statistical analysis confirms that the three primary transformant groups with high expression levels of SC-1 all have statistically significantly higher Brix levels than those of the untransformed control Flora-Dade.

In contrast, the transformants with low expression levels of the EGTom2-gene (EGTom2-2, EGTom2-8, EGTom2-11, and EGTom2-26) all have Brix levels ranging from 3 to 3.5, less than the Flora-Dade control. Again, statistical analysis confirms that these plants with low expression levels of EGTom2—all have statistically significantly lower Brix levels that the Flora-Dade control.

Finally, the EGTom2-21 transformants (which showed intermediate levels of gene expression) have Brix levels close to that of the Flora-Dade control, midway in Brix values between the sweetest and the less sweet transformants.

These results show that higher expression levels of EGTom2 cause transformed tomato plants to exhibit higher Brix values (i.e., greater sweetness).

Example 5. Identification of Orthologs from Cultivated Tomato

The sequences of EGTom1 and EGTom2 were used to identify orthologs in cultivated tomato (*Solanum esculentum*).

Cultivated tomato (*Solanum esculentum*) mRNA with partial 3' UTR (salt/drought tolerance) (SEQ ID NO: 3):

```
atgGAGAATAATAAAGGAAATGCTGAGAGTAATGAGGACAGTCATATCA
CACCCAGCACGAAGAAAACTCACGCGCTTCAACAAAATGGCGTGGAGAA
```

-continued

```
TATAGAGGTGCCCCCCAACTCTGATGCGACTAAAAAAAAGGGCCCCAGT
AGAAGTGCCAAGAGAAAATCTGCTAAAAGGCGATGGTTGCGAGAGATGG
CCAAAATTAAGGAGAAGAATGCAGATGCTGAATCGGAAGGGCTGCGGAA
CTGGAAAGAAATGCAGGCTAAAGCTGGAAAGGGAGAGCCTAGCTGCCAA
CCAAAGGGGCGATTGAATGACGGGGCTAATGGTCACCGAAATGGGAAGC
AGCAGATAACTAAAACTAAAAAAGAAGAGGTAACTGGCCAACCAAAGGG
ACTTCTGCATAGGAAGCAATTCCATAGTGAAGATAAGAATGGAGATACA
AACGAAGAAAAGCAAGCAGAAGAGAAAAGCAAATCATGTGGACAATCAT
GTCAAAATAGTGACTCAGAAGATGAAGTTGTTCCAGTTGAAATAAGGCC
TGGGCATATTCGCTTTGAACCTGTTGGAAAAGAACAAGTTTCAAAGCAG
AGTCAAGAAGAAATGGAAAGTTTCAAGTGGAATGGTATGATGAGCAAGA
AAAAGGGACAGAAATGGGGCCAAGAGAAAGTTTCATTTCCCCAAAAGAC
TGATTCTCTAGGTTCAAACAAAGAATATCCTGATATGATGAGTCGTGAG
AGACAGAAATGGATCCAAGAGAAAGACTCATTTTCCCAAAAGAATGATT
CCCTTAGTTCAAACAAAGAACATCCTGAGATAATGAATCGTAAAAGACA
GAAATGGGGCCAAGAGAATATTTCATTTGCCCAAAAGAATGATTCTCCA
GGTTCAAGCAAAGAACATCCTGATATGATGAACCGTGAGAGACAGAAAT
GGAGCCAAGAGAAAAACTTGTTTTACCAAAAGAATGATTCTCTCGGTTC
AAACAAAGAACATCCCGAGATAATGAATCGTAATAGACAGAACTGGGGC
GAAGAGAATGTTTCATTTTCCCAAAAGAATGATTCTCTAGATTCAAACA
AAAAACATCCTGAGATGTTGAATGGTGAAAAGGAGCCTCATTTCAATGG
ATCAATTGACTTCAATACGCTTCCTTTTCTTTCTGGCCAGCCCAAGGAA
GGTCTTGTGATTGCATATCGGCTGCTTGAGTTATCATCAACCTGGACCC
CTGAAGTTTCCTCCTATCGGGTTGGGAAAATATCATCGTATAATTCTGA
AGCAAATAGAGTTTTGCTGATGCCAGTAGCTGAATTTCCAGTCATTTGT
ACTGAGGATGAGTCTTCAAAGCAACCAGATAGCTCTATTTATAATGAAG
ACGGATCTTTGGAGATAGAATTTTCAGCGCTTCTTGAAGTTCGTCTGAT
GAATAGTACTCCAGATCAAGGAGTACATGAAGGGGTTATTGAGGGTTCT
GCTGCCAATGAGTCCACTCCAGTGCTTGGAAGCAGTAAAAAGAAAAATG
AAACTCCAGTTCCTGGAGCTGGAGAAGTAAGCAATGGAAAACAAACACG
ATCTACCCCTTCAGAAAATGGCGGAGTAAACCTGTGGGAGCAATTCAGT
GATACTCTAAAGTCCAAGAAGGCAGAATTAGCTCAGGAAAGTAATTGGG
ATAAGGCAAGTACTGGAAAGAGCCCTTGGTCATATCGACCCATGAGAGG
CACTGCGCTAGGCCCTACAATGGCCTTCCTTAGATCCCAAAAGAAAATA
taaGATGAAGTTGCAGTTGCATATTTTGTTCATATTATCGTATATTAAC
CCGTTTCATTCTCTTTAAGTTTTGCAAAATTCT
```

Cultivated tomato (*Solanum esculentum*) coding sequence (salt/drought tolerance) (SEQ ID NO: 4):

```
atgGAGAATAATAAAGGAAATGCTGAGAGTAATGAGGACAGTCATATCA
CACCCAGCACGAAGAAAACTCACGCGCTTCAACAAAATGGCGTGGAGAA
TATAGAGGTGCCCCCCAACTCTGATGCGACTAAAAAAAAGGGCCCCAGT
AGAAGTGCCAAGAGAAAATCTGCTAAAAGGCGATGGTTGCGAGAGATGG
```

-continued

CCAAAATTAAGGAGAAGAATGCAGATGCTGAATCGGAAGGGCTGCGGAA

CTGGAAAGAAATGCAGGCTAAAGCTGGAAAGGGAGAGCCTAGCTGCCAA

CCAAAGGGGCGATTGAATGACGGGGCTAATGGTCACCGAAATGGGAAGC

AGCAGATAACTAAAACTAAAAAAGAAGAGGTAACTGGCCAACCAAAGGG

ACTTCTGCATAGGAAGCAATTCCATAGTGAAGATAAGAATGGAGATACA

AACGAAGAAAAGCAAGCAGAAGAGAAAAGCAAATCATGTGGACAATCAT

GTCAAAATAGTGACTCAGAAGATGAAGTTGTTCCAGTTGAAATAAGGCC

TGGGCATATTCGCTTTGAACCTGTTGGAAAAGAACAAGTTTCAAAGCAG

AGTCAAGAAGAAATGGAAAGTTTCAAGTGGAATGGTATGATGAGCAAGA

AAAAGGGACAGAAATGGGGCCAAGAGAAAGTTTCATTTCCCCAAAAGAC

TGATTCTCTAGGTTCAAACAAAGAATATCCTGATATGATGAGTCGTGAG

AGACAGAAATGGATCCAAGAGAAAGACTCATTTTCCCAAAAGAATGATT

CCCTTAGTTCAAACAAAGAACATCCTGAGATAATGAATCGTAAAAGACA

GAAATGGGGCCAAGAGAATATTTCATTTGCCCAAAAAGAATGATTCTCC

AGGTTCAAGCAAAGAACATCCTGATATGATGAACCGTGAGAGACAGAAA

TGGAGCCAAGAGAAAAACTTGTTTTACCAAAAGAATGATTCTCTCGGTT

CAAACAAAGAACATCCCGAGATAATGAATCGTAATAGACAGAACTGGGG

CGAAGAGAATGTTTCATTTTCCCAAAAGAATGATTCTCTAGATTCAAAC

AAAAAACATCCTGAGATGTTGAATGGTGAAAAGGAGCCTCATTTCAATG

GATCAATTGACTTCAATACGCTTCCTTTTCTTTCTGGCCAGCCCAAGGA

AGGTCTTGTGATTGCATATCGGCTGCTTGAGTTATCATCAACCTGGACC

CCTGAAGTTTCCTCCTATCGGGTTGGGAAAATATCATCGTATAATTCTG

AAGCAAATAGAGTTTTGCTGATGCCAGTAGCTGAATTTCCAGTCATTTG

TACTGAGGATGAGTCTTCAAAGCAACCAGATAGCTCTATTTATAATGAA

GACGGATCTTTGGAGATAGAATTTTCAGCGCTTCTTGAAGTTCGTCTGA

TGAATAGTACTCCAGATCAAGGAGTACATGAAGGGGTTATTGAGGGTTC

TGCTGCCAATGAGTCCACTCCAGTGCTTGGAAGCAGTAAAAAGAAAAAT

GAAACTCCAGTTCCTGGAGCTGGAGAAGTAAGCAATGGAAAACAAACAC

GATCTACCCCTTCAGAAAATGGCGGAGTAAACCTGTGGGAGCAATTCAG

TGATACTCTAAAGTCCAAGAAGGCAGAATTAGCTCAGGAAAGTAATTGG

GATAAGGCAAGTACTGGAAAGAGCCCTTGGTCATATCGACCCATGAGAG

GCACTGCGCTAGGCCCTACAATGGCCTTCCTTAGATCCCAAAAGAAAAT

Ataa

Cultivated tomato (*Solanum esculentum*) candidate mRNA with partial UTR (fruit sugar content/sweetness) (SEQ ID NO: 5):

CATGGTGAAGGATTTTAGTGAGGGATAAGAAGCTACGATAT<u>atg</u>GAGAA

TTCGCGTGAGTTTCTAAGCAATGGAAAACCAGCTGATCCTGGTCTTCAA

ATTATAAGGCACCCCTCTTACCAATCTTGTGGGAAATTATCGTTATCTT

GGTTTGATATTAGAGTCTTTTACATCAGAATCAGCAATTTTATGGTCGA

TGATTCAACCCCAGAAAGTCTTACGCTTAACCATATCCCTCTAAGCCCC

GATACACTGCTTGAAGTTAATGGTAAAAGATGTTCAGTGTACTCAGAAG

GAGCCTCTTGCTTTCTTCGAAGGGACCGTGTTGATAAGAAAGCTGAAGA

AGCTACATTTGTGAGCACAGATAGTATAAGATTGACTGGGAGTGTGAAC

TTTGAGGTTTCATATAAAGATGATCTTTTTCTCTCTGGGACTTTGGAGA

TGGCCAACATCAATGATTCTCAAAACTGTCTTAGGAGATGGAGCATGAA

CTGTGAATCAGTTATGAGTGCTGGCACGGGATTTCTGAAAGGAAAACAT

ATTGTGGGTTCTGAATCATTGTCACCGACAATTGAAGTGTATGTTACTG

GTTGCTTCTCTGGGACACCTATCATCTTAACTAAGACTTTGCAGCTAAA

TCACAGGAAGAAGCACCATAGAAAGGGTATGTTGGACTCCATTCCGGAG

CATGACACATCTGAACAGCATAAAGAAGTCTCATCTGAACATGATCTGC

AGGTAACAGAATACAACGGAAACTACAAACCAGAAAGCGAAGAAGACTA

CAACAACATGTACTGGGGACGAACAGAACTTATGGATGGTGAAGACGGA

GAAATGTCCTGGTTCAATGCTGGGGTTCGAGTTGGTGTTGGGATTGGCC

TTGGCATTTGTGTAGGAGTTGGAGTAGGAGTTGGTTTATTAGTCCGTAC

TACACGAAACTTAAGAAGGCGCCTTATGtaaTTACATAGCATACATATA

AAAGGCTAACAATACAGAGATGCTGTTTTTAAG

Cultivated tomato (*Solanum esculentum*) coding sequence (fruit sugar content/sweetness) (SEQ ID NO: 6):

<u>atg</u> GAG AAT TCG CGT GAG TTT CTA AGC AAT GGA AAA

CCA GCT GAT CCT GGT CTT CAA ATT ATA AGG CAC CCC

TCT TAC CAA TCT TGT GGG AAA TTA TCG TTA TCT TGG

TTT GAT ATT AGA GTC TTT TAC ATC AGA ATC AGC AAT

TTT ATG GTC GAT GAT TCA ACC CCA GAA AGT CTT ACG

CTT AAC CAT ATC CCT CTA AGC CCC GAT ACA CTG CTT

GAA GTT AAT GGT AAA AGA TGT TCA GTG TAC TCA GAA

GGA GCC TCT TGC TTT CTT CGA AGG GAC CGT GTT GAT

AAG AAA GCT GAA GAA GCT ACA TTT GTG AGC ACA GAT

AGT ATA AGA TTG ACT GGG AGT GTG AAC TTT GAG GTT

TCA TAT AAA GAT GAT CTT TTT CTC TCT GGG ACT TTG

GAG ATG GCC AAC ATC AAT GAT TCT CAA AAC TGT CTT

AGG AGA TGG AGC ATG AAC TGT GAA TCA GTT ATG AGT

GCT GGC ACG GGA TTT CTG AAA GGA AAA CAT ATT GTG

GGT TCT GAA TCA TTG TCA CCG ACA ATT GAA GTG TAT

GTT ACT GGT TGC TTC TCT GGG ACA CCT ATC ATC TTA

ACT AAG ACT TTG CAG CTA AAT CAC AGG AAG AAG CAC

CAT AGA AAG GGT ATG TTG GAC TCC ATT CCG GAG CAT

GAC ACA TCT GAA CAG CAT AAA GAA GTC TCA TCT GAA

CAT GAT CTG CAG GTA ACA GAA TAC AAC GGA AAC TAC

AAA CCA GAA AGC GAA GAA GAC TAC AAC AAC ATG TAC

TGG GGA CGA ACA GAA CTT ATG GAT GGT GAA GAC GGA

GAA ATG TCC TGG TTC AAT GCT GGG GTT CGA GTT GGT

GTT GGG ATT GGC CTT GGC ATT TGT GTA GGA GTT GGA

-continued

```
GTA GGA GTT GGT TTA TTA GTC CGT ACT ACA CGA AAC

TTA AGA AGG CGC CTT ATG taa
```

Example 6. Analysis of Orthologs of Positively Selected Genes in Other *Solanum* Species Other members of the genus *Solanum* have phenotypic traits with agronomic and commercial value. These traits appear to be the result of adaptation (Moyle, 2008) so the analysis can be directed to additional species of *Solanum*. For example, *S. chilense* is known to be very drought tolerant, an adaptive response to its restricted habitat: the hyperarid coastal deserts of South America between Peru and Chile (Moyle, 2008). Thus, because this species is not salt tolerant, it provides a model that will allow teasing out of drought tolerance from salt tolerance. *S. peruvianum* is notably resistant to both insects and disease (Moyle, 2008). *S. neorickii* is a widespread, robust species that thrives in a diverse range of habitats (Moyle, 2008); it appears to be generalist species that competes well and is robust to environmental variation, traits that could be useful to integrate into crop species.

Because Ka/Ks analysis is performed in a pairwise framework, when positively selected genes are identified, it is not a priori clear on which lineage positive selection has occurred. Outgroup analysis answers this question; thus orthologs of the two candidate genes were amplified from wild species of the genus *Solanum*. The EGTom1 and EGTom2 genes were examined in multiple accessions from the following wild tomato species: *Solanum peruvianum, S. corneliomulleri, S. neorickii, S. galapagense, S. arcanum, S. habrochaites, S. chilense, S. lycopersicum, S. pennellii, S. chmielewskii, S. huaylasense, S. lycopersicoides, S. sitiens*, and *S. ochranthum*. [Germplasm from these *Solanum* species was obtained from the C.M. Rick Tomato Genetics Resource Center (TGRC)].

Outgroup analysis was then used to establish that both EGTom1 and EGTom2 were positively selected on the Galapagos tomato lineage. In addition, allelic diversity was characterized for EGTom1 and EGTom2 from these accessions of *Solanum* species. Allelic diversity was found to be high for both identified genes in the other wild tomato species, but is almost non-existent in the Galapagos tomato. This result is consistent with the idea that these two genes underwent severe bottle-necking during the episode of adaptive speciation that gave rise to the Galapagos tomato, *S. cheesmaniae*. This is further evidence that these two genes have changed in a unique fashion in this species, resulting in new phenotypic traits.

Example 7. Analysis of Tomato Orthologs of EG Domestication Genes Identified from Other Species Six positively selected rice domestication genes were previously identified that showed associations with yield and/or other agronomic traits in rice (data not provided herein). The orthologs of some of these genes were found to be independently selected during the domestications of corn, barley and sorghum (data not provided herein). Thus, it is hypothesized that a few key genes are open to change during selective events, and that these same genes often are key control points for important adaptive traits. Given that these genes have been selected independently during several independent domestications that occurred at different times, in several different locations scattered across the planet, the question was whether the orthologs of any of these genes were also selected during domestication of the tomato. Using sequence databases putative tomato orthologs were identified for four of these positively selected rice genes. These putative orthologs from cultivated and Galapagos tomatoes were amplified, sequenced, and phylogenetic tree-building was performed to confirm orthology (while being cognizant of issues of paralogy and gene duplication).

Ka/Ks analysis was performed on confirmed orthologs to determine if any were positively selected in tomatoes. None of the four were positively selected in tomato. This result suggests that while independent adaptive evolution has occurred at the same six loci in the monocot grass family (i.e., in corn, barley, wheat, and rice), the dicots must have followed a different trajectory during domestication. This makes clear the value of searching for positive selection in multiple models: the monocot grasses, the dicot tomato, and other commercially valuable dicot crop species as well.

Example 8. Validation of Gene Function

Many Galapagos tomato accessions were collected from carefully documented habitats that differ significantly in terms of salinity and moisture. These accessions were obtained from the Tomato Genetics Resource Center (TRGC; located at the University Of California, Davis) and were genotyped.

Alleles will be mapped for each candidate gene to aspects of the habitat from which the accessions were collected: moisture and salinity and each accession were classified as xeric, mesic, or hydric, as well as saline or freshwater.

Very little allelic diversity was found to exist in Galapagos tomato for either EGTom1 or EGTom2. As a control, two non-selected (conserved) genes were genotyped and substantial allelic diversity was found for each of the controls.

When considered in light of the extensive allelic diversity found for other candidate genes in other the wild tomato species, this is evidence for the role of positive selection in creating new functions for EGTom1 and EGTom2.

Example 9. Studies of all 55 Accessions of Galapagos Tomato

Fifty five (55) accessions of Galapagos tomato were obtained from the TRGC. The geographic locations where these accessions were originally collected are well documented.

The tiny seeds of Galapagos tomato did not easily yield DNA. Isolation of DNA is facilitated by germinating seeds to seedling stage. RNA isolation from Galapagos tomato is also facilitated by use of seedlings, as these seedlings express a wide array of the plant's genes, and yield large quantities of total RNA. These seedlings were on dampened filter paper. Some seeds required treatment with dilute HCL to initiate germination.

Seedlings were flash-frozen in liquid $N_2$, and then total RNA and genomic DNA were isolated from each seedling with protocols and kits used on our lab for many years with consistent success.

Each candidate gene was genotyped. The same PCR thermocycling conditions and amplification primers were used for all 55 accessions; this allowed all reactions to be done in a 96-well plate format, for both time and cost savings.

Detailed geographic and habitat data are available for the Galapagos Islands from several sources, including the Charles Darwin Research Station (CDRS), Santa Cruz, Galapagos; the Tomato Genetics Resource Center, and the Germplasm Resources Information Network (GRIN). These data were plotted against the physical locations (using GPS data) from which each Galapagos tomato accession was collected using the Google Earth software package (version 5).

For each tomato accession each candidate gene was genotyped. The plan was to use the particular allele(s) from each accession to plot against the habitat data for moisture and salinity. However, as described above, both EGTom1 and EGTom2 lack allelic diversity (unlike conserved Galapagos tomato genes examined as controls, which show high levels of allelic diversity). Thus, no association was found between allele-type and habitat type due to the lack any allelic diversity. This leads to the conclusion that this is a result of the very strong selective pressures that altered the functions of these genes.

Example 10. Tomato Breeding with Tomato Plants Expressing EGTom1 and/or EGTom2

A 'Micro-Tom' tomato plant with a conferred copy of the coding sequence for EGTom1 and/or EGTom2 as obtained in Example 3 or 4 can be crossed to a plant of the 'Early Girl' or 'Big Boy' tomato varieties and the resultant progeny can be tested for salt/drought tolerance and sugar content/sweetness of the fruit.

The presence of the EGTom1 and/or EGTom2 polynucleotide can be confirmed in the resultant 'Early Girl' progeny according to the procedures set forth elsewhere herein.

In a further procedure, the transformed 'Early Girl' or 'Big Boy' tomato plants can be backcrossed one or more times to 'Early Girl' and 'Big Boy', respectively, to produce a near isogenic or isogenic 'Early Girl' or 'Big Boy' tomato with the coding sequence for EGTom1 and/or EGTom2.

Example 11. Transformation of Grape Plant with EGTom Grape Ortholog

The candidate EGTom grape ortholog (SEQ ID NO: 13) will be cloned into appropriate expression vectors for use in transgenic grapes such as 'Sugrone', 'Crimson Seedless', or other transformable grape variety.

Transgenic grape varieties will be prepared using the EGTom grape ortholog identified in Example 2 (SEQ ID NO: 13, or sequences encoding the EGTom peptide sequence of SEQ ID NO: 14) and the impact of specific alleles will be measured on drought/salt-tolerance, and fruit sugar content, respectively.

Grape plants can be transformed with a construct containing EGTom from grape or any of the herein identified EGtom homologs, orthologs and paralogs using standard transformation technology for grape plants. See. e.g., Li et al (2008) "An improved protocol for *Agrobacterium*-mediated transformation of grapevine (*Vitis vinifera* L.)" Plant Cell Tiss Organ Cult; Perl et al (1996) "Establishment of an *Agrobacterium*-mediated transformation system for grape (*Vitis vinifera* L.): The role of antioxidance during grape-*Agrobacterium* interactions" Nat Bio 14 624-628.

The EGTom-transformed grape plants can be tested for salt/drought tolerance and the EGTom-transformed grape plants can be tested for fruit sugar content compared to the untransformed, control grape plants.

Example 12. Grape Breeding with Grape Plants Expressing EGTom

A grape plant with a conferred copy of the coding sequence for EGTom as described in Examples 2 and 11 (SEQ ID NO: 13, and SEQ ID NO: 14) can be crossed to a commercially relevant grape plant such as the varieties 'Crimson Seedless', 'Einset', or 'Diamond', and the resultant progeny can be tested for salt/drought tolerance and sugar content/sweetness of the fruit.

The presence of the EGTom polynucleotide can be confirmed in the resultant 'Crimson Seedless' (or other bred variety) progeny according to the procedures set forth elsewhere herein.

In a further procedure, the transformed 'Crimson Seedless', or 'Einset' grape plants can be backcrossed one or more times to 'Crimson Seedless', or 'Einset', respectively, to produce a near isogenic or isogenic 'Crimson Seedless', or 'Einset' grape with the coding sequence for EGTom.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, patent publications, and nucleic acid and amino acid sequences cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

ADDITIONAL REFERENCES

Alleweldt et al., (1988) Progress in grapevine breeding. Theoretical and Applied Genetics Vol 75:5 669-673

Alpert, K. A. Grandillo, S., and Tanksley, S. D. (1995) fw2.2: a major QTL controlling fruit weight is common to both red- and green-fruited tomato species. *Theor. Appl. Genet.* 91: 994-1000.

Collins A., Morton N. E. (1998) Mapping a disease locus by allelic association. *Proc. Natl. Acad. Sci. USA,* 95, 1741-1745.

Darwin, C. (1859) *On the Origin of Species by Means of Natural Selection, or The Preservation of Favoured Races in the Struggle for Life.*

Darwin, S. C., Knapp, S. and Peralta, I. E. (2003) Taxonomy of tomatoes in the Galapagos Islands: Native and introduced species of *Solanum* section *Lycopersicon* (*Solanaceae*). *Syst. and Biodiversity.* 12: 29-53.

Flowers, T. J. (2004) Improving crop salt tolerance. *J. Exp. Bot.* 55(396): 307-319.

Frary, A., Nesbitt, T. C., Frary, A., Grandillo, S., van der Knaap, E. (2000) fw2.2: a quantitative trait locus key to the evolution of tomato fruit size. *Science* 289: 85-88.

Grandillo, S., Ku, H. M., and Tanksley, S. D. (1999) Identifying the loci responsible for natural variation in fruit size and shape in tomato. *Theor. Appl. Genet.* 99: 978-987.

Jaillon et al., (2007) The grapevine genome sequence suggests ancestral hexaploidization in major angiosperm phyla. Nature, 449:463-467

Li, W.-H., Wu, C.-I., and Luo, C.-C. (1985) *Mol. Biol. Evol.* 2: 150-174.

Li, W.-H. (1993) *J. Mol. Evol.* 36: 96-99.

Li et al., (2008) An improved protocol for *Agrobacterium*-mediated transformation of grapevine (*Vitis vinifera* L.). Plant Cell Tiss Organ Cult.

Messier, W. and Stewart, C.-B. (1994) *Current Biology* 4: 911-913.

Messier, W. and Stewart, C.-B. (1997) *Nature* 385: 151-154.

Messier, W. and Sikela, J. M. (2001) Methods to identify evolutionarily significant changes in polynucleotide and polypeptide sequences in domesticated plants and animals. U.S. Pat. No. 6,274,319.

Morton N. E., Zhang W., Taillon-Miller P., Ennis S., Kwok P., Collins A. (2001) The optimal measure of allelic association. *Proc. Natl. Acad. Sci. USA,* 98, 5217-5221.

Moyle, L. S. (2008) Ecological and evolutionary genomics in the wild tomatoes (*Solanum* Sect. *Lycopersicon*). *Evolution* 62(12): 2995-3013.

Munns, R. and Tester, M. (2008) Mechanisms of salt tolerance. *Ann. Rev. Plant Biol.* 59: 651-681.

Nei, M. and T. Gojobori (1986) Simple methods for estimating the numbers of synonymous and nonsynonymous nucleotide substitutions. *Mol. Biol. Evol.* 3: 418-426.

Nesbitt, T. C. and Tanksley, S. D. (2002) Comparative sequencing in the genus *Lycopersicon*: implications for the evolution of fruity size in the domestication of cultivated tomatoes. *Genetics* 162: 365-379.

Nuez, F., Prohens, J., and Blanca. J. M. (2004) Relationships, origin, and diversity of Galapagos tomatoes: implications for the conservation of natural populations. *Amer. J. Bot.,* 91(1); 86-99.

Peralta, I. E. and Spooner, D. M. (2001) Granule-bound starch synthase (GBSSI) gene phylogeny of wild tomatoes (*Solanum* L. section *Lycopersicon* [Mill] WTTST subsection *Lycoperiscon. Amer. J. Bot.,* 88(10): 1888-1902.

Peralta, I. E., Knapp, S., and Spooner, D. M. (2006) Nomenclature for wild and cultivated tomatoes. *TGC Report* 56: 1-12.

Perl et al (1996) Establishment of an *Agrobacterium*-mediated transformation system for grape (*Vitis vinifera* L.): The role of antioxidance during grape-*Agrobacterium* interactions. Nat Bio 14 624-628

Reisch et al., (1993) Wine and Juice Grape Varieties for Cool Climates. Cornell Cooperative Information Bulletin 233

Rush, D. W. and Epstein, E. (1976) Genotypic responses to salinity: differences between salt-sensitive and salt-tolerant genotypes of the tomato. *Plant Physiol.* 57: 162-166.

Sairam, R. K. and Tyagi. A. (2004) Physiology and molecular biology of salinity stress tolerance in plants. *Current Sci.* 86(3): 407-421.

Swanson, W. J., Vacquier, V. D. (1995) *Proc. Natl. Acad. Sci.* 92: 4957-4961.

Swanson. W. J., Vacquier, V. D. (1998) *Science* 281:712.

Swanson. W. J., Yang, Z., M. F. Wolfner, M. F., C. F. Aquadro, C. F. (2001) Positive Darwinian selection drives the evolution of several female reproductive proteins in mammals." *Proc. Natl. Acad. Sci. USA* 98(5): 2509-2514.

Tanji, J. J. (ed.) (1990) *Agricultural Salinity Assessment and Management*, American Society of Civil Engineers.

Zeigler, R., quoted in Rice, A. (2008) Is there such a thing as agro-imperialism?*New York Times Magazine, Nov.* 22, 2009.

Zondervan K. T., Cardon L. R. (2004) The complex interplay among factors that influence allelic association. *Nature Reviews, Genetics,* 5, 89-100.

The invention claimed is:

1. A transgenic tomato plant, plant part, plant cell, or plant tissue culture comprising a construct comprising a nucleic acid encoding an EGTom2 polypeptide having at least 95% sequence identity to SEQ ID NO 8; wherein said transgenic tomato plant, or transgenic tomato plant produced from said plant part, plant cell, or plant tissue culture, expresses said EGTom2-encoding nucleic acid at a level of at least 300 copy/ng RNA as determined by quantitative real-time RT-PCR, and has increased fruit sweetness compared to the fruit of an untransformed control tomato plant.

2. A tomato fruit produced by the transgenic tomato plant, of claim 1, wherein the tomato fruit comprises the nucleic acid encoding the EGTom2 polypeptide having at least 95% sequence identity to SEQ ID NO 8.

3. The transgenic tomato plant, plant part, plant cell, or plant tissue culture, of claim 1, wherein the construct further comprises a gene termination sequence.

4. The transgenic tomato plant, plant part, plant cell, or plant tissue culture, of claim 1, wherein the construct further comprises a promoter.

5. The transgenic tomato plant, plant part, plant cell, or plant tissue culture, of claim 1, wherein the construct is an overexpression construct.

6. A method for producing a transgenic tomato plant with increased fruit sweetness, said method comprising:

(i) transforming a tomato plant cell with a construct comprising a nucleic acid sequence encoding a EGTom2 polypeptide having at least 95% identity to SEQ ID NO 8; and (ii) cultivating the transgenic tomato cell under conditions conducive to regeneration and mature plant growth;

wherein the transgenic tomato plant regenerated from said transgenic plant cell expresses said EGTom2-encoding nucleic acid at a level of at least 300 copy/ng RNA as determined by quantitative real-time RT-PCR, and has increased fruit sweetness compared to the fruit of untransformed control tomato plants.

7. The method of claim 6, wherein the construct is an over expression construct.

8. A method of producing hybrid tomato seed, said method comprising: crossing the transgenic tomato plant of claim 1 with another tomato plant, and harvesting the resultant seed.

9. An F1 hybrid plant grown from the seed produced by the method of claim 8, wherein the F1 hybrid plant comprises the polynucleotide from the transgenic tomato plant.

10. A transgenic tomato plant of claim 1, wherein the plant is a cultivated tomato plant (*Solanum esculentum*).

11. The transgenic tomato plant, plant part, plant cell, or plant tissue culture of claim 1, wherein the nucleic acid sequence encodes an EGTom2 polypeptide having at least 96% sequence identity to SEQ ID No 8.

12. The transgenic tomato plant, plant part, plant cell, or plant tissue culture of claim 1, wherein the nucleic acid sequence encodes an EGTom2 polypeptide having at least 97% sequence identity to SEQ ID No 8.

13. The transgenic tomato plant, plant part, plant cell, or plant tissue culture of claim 1, wherein the nucleic acid sequence encodes an EGTom2 polypeptide having at least 98% sequence identity to SEQ ID No 8.

14. The transgenic tomato plant, plant part, plant cell, or plant tissue culture of claim 1, wherein the nucleic acid sequence encodes an EGTom2 polypeptide having at least 99% sequence identity to SEQ ID No 8.

* * * * *